US012344886B2

(12) United States Patent
Meller et al.

(10) Patent No.: US 12,344,886 B2
(45) Date of Patent: Jul. 1, 2025

(54) COMPOSITIONS AND METHODS FOR DETECTION OF GENOMIC VARIATIONS

(71) Applicant: TECHNION RESEARCH & DEVELOPMENT FOUNDATION LIMITED, Haifa (IL)

(72) Inventors: Amit Meller, Haifa (IL); Michelle Patkin, Haifa (IL); Tal Gilboa, Haifa (IL); Yana Ben Zvi Rozevsky, Kiryat Motzkin (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 522 days.

(21) Appl. No.: 16/621,812

(22) PCT Filed: Jun. 14, 2018

(86) PCT No.: PCT/IL2018/050659
§ 371 (c)(1),
(2) Date: Dec. 12, 2019

(87) PCT Pub. No.: WO2018/229774
PCT Pub. Date: Dec. 20, 2018

(65) Prior Publication Data
US 2020/0216881 A1 Jul. 9, 2020

Related U.S. Application Data

(60) Provisional application No. 62/519,966, filed on Jun. 15, 2017.

(51) Int. Cl.
*C12Q 1/6816* (2018.01)
*C12Q 1/6827* (2018.01)
*G01N 33/487* (2006.01)

(52) U.S. Cl.
CPC ......... *C12Q 1/6816* (2013.01); *C12Q 1/6827* (2013.01); *G01N 33/48721* (2013.01); *C12Q 2521/501* (2013.01); *C12Q 2563/179* (2013.01); *C12Q 2565/631* (2013.01)

(58) Field of Classification Search
CPC .................................. C12Q 1/68; C07H 21/00
See application file for complete search history.

(56) References Cited

U.S. PATENT DOCUMENTS

| | | | | |
|---|---|---|---|---|
| 4,988,617 A * | 1/1991 | Landegren | ........... | C12Q 1/6827 536/78 |
| 5,484,909 A * | 1/1996 | Nietupski | ........... | C12Q 1/689 435/6.12 |
| 5,871,921 A * | 2/1999 | Landegren | ........... | C12Q 1/6813 435/6.12 |
| 7,300,755 B1 * | 11/2007 | Petersdorf | ........... | C12Q 1/6813 435/6.12 |
| 2003/0032087 A1 * | 2/2003 | Challita-Eid | ........... | C07K 14/47 435/7.1 |
| 2003/0219765 A1 * | 11/2003 | Costa | ........... | C12Q 1/6827 435/6.14 |
| 2004/0077828 A1 * | 4/2004 | Rubin | ........... | C07K 14/71 530/328 |
| 2006/0063196 A1 * | 3/2006 | Akeson | ........... | G01N 33/48721 435/7.1 |
| 2006/0094019 A1 * | 5/2006 | Selvin | ........... | C12Q 1/6827 536/25.32 |
| 2008/0090733 A1 * | 4/2008 | Dapprich | ........... | C12Q 1/6834 506/3 |
| 2009/0202993 A1 * | 8/2009 | Lagunavicius | ........... | C12Q 1/6841 435/6.12 |
| 2010/0081147 A1 * | 4/2010 | Ho | ........... | C12Y 201/01006 536/23.1 |
| 2012/0021930 A1 * | 1/2012 | Schoen | ........... | C12Q 1/6865 506/9 |
| 2012/0252686 A1 * | 10/2012 | Umbarger | ........... | C12Q 1/6874 506/9 |
| 2014/0113873 A1 * | 4/2014 | Guillemin | ........... | G01N 33/57419 435/375 |
| 2014/0120534 A1 * | 5/2014 | Bernitz | ........... | C12Q 1/6809 435/6.11 |
| 2017/0173021 A1 * | 6/2017 | Lowe | ........... | G01N 33/57438 |
| 2017/0211133 A1 * | 7/2017 | Landegren | ........... | C12Q 1/6876 |

FOREIGN PATENT DOCUMENTS

| | | | |
|---|---|---|---|
| WO | 2005026389 | A2 | 3/2005 |
| WO | 2009092035 | A3 | 7/2009 |
| WO | 2014165267 | A2 | 10/2014 |

OTHER PUBLICATIONS

Baner et al. Nucleic Acids Research 31(17) :e103 (Year: 2003).*
Wilson et al. Analytical Chemistry 91 :6783 (Year: 2019).*
Stratagene Catalog 1988.*
Hong et al., Genome Biology 15:517 (Year: 2014).*
Li et al. GigaScience 5:34 (Year: 2016).*
Maitra et al., Electrophoresis 33:3418-3428 (Year: 2012).*
Shaw, Greg. BJU International 112: 664-665 (Year: 2013).*
Travers et al., Nucleic Acids Research 38(15) : e159 (Year: 2010).*
Schouten et al., Relative quantification of 40 nucleic acid sequences by multiplex ligation-dependent probe amplification. Nucleic Acids Research 30(12) : e57 (Year: 2002).*
Debeljak et al., J. of Molecular Diagnostics 16(5) : 496-503 (Year: 2014).*
Ortiz et al., Molecular and Cellular Probes12 : 219-226 (Year: 1998).*

(Continued)

*Primary Examiner* — Ethan C Whisenant
(74) *Attorney, Agent, or Firm* — The Roy Gross Law Firm, LLC; Roy Gross

(57) ABSTRACT

The present invention concerns compositions, kits and methods for genetic variation detection and classification. These methods combine the specificity of a ligation reaction with the single-molecule sensitivity of nanopore biosensors. This invention can achieve clinical detection of many diseases, including bacterial infections and cancer entities, by identification of specific genetic alterations.

16 Claims, 8 Drawing Sheets
(6 of 8 Drawing Sheet(s) Filed in Color)
Specification includes a Sequence Listing.

(56) References Cited

OTHER PUBLICATIONS

Schouten et al., Nucleic Acids Research 30(12) : e 57 (Year: 2002).*
Ellis et al., Simultaneous and sensitive detection of human immunodeficiency virus type 1(HIV) drug resistant genotypes by multiplex oligonucleotide ligation assay Journal of Virological Methods 192: 39-43 (Year: 2013).*
U. Landegren et al., "A ligase-mediated gene detection technique", Science, vol. 241 pp. 1077-1080, 1988.
Sho Watanabe et al., "Microbead-based ligase detection reaction assay using a molecular beacon probe for the detection of low-abundance point mutations", Analytical chemistry vol. 86 Issue 1 pp. 900-906, 2013.
Meni Wanunu et al., "Electrostatic focusing of unlabelled DNA into nanoscale pores using a salt gradient", Nature hanotechnology vol. 5 pp. 160-165, 2010.
Evrim Atas et al., "DNA sequencing and bar-coding using solid-state nanopores", Electrophoresis vol. 33 Issue 23 pp. 3437-3447, 2012.
Ossama Assad et al., "Two color DNA barcode detection in photoluminescence suppressed silicon nitride nanopores", Nano letters vol. 15 Issue 1 pp. 745-752, 2014.
Ben McNally et al., "Optical recognition of converted DNA nucleotides for single-molecule DNA sequencing using hanopore arrays", Nano letters vol. 10 Issue 6 pp. 2237-2244, 2010.
Yan Shan Ang and Lin-Yue Lanry Yung, "Rapid and Label-Free Single-Nucleotide Discrimination via an Integrative NanoparticleNanopore Approach", ACS Nano, vol. 6 Issue 10 pp. 8815-8823, 2012.
Tal Gilboa and Amit Meller, "Optical sensing and analyte manipulation in solid-state nanopores", The Analyst, Issue 140 vol. 14, pp. 4733-4747, 2015.
Marie A. Iannone et al., "Multiplexed Single Nucleotide Polymorphism Genotyping by Oligonucleotide Ligation and Flow Cytometry", Cytometry, Issue 39 vol. 2 pp. 131-140, 2000.
Jinglin Kong et al., "Single Molecule Based SNP Detection Using Designed DNA Carriers and Solid-State Nanopores", Chemical Communications, Issue 53 vol. 2, 2016.
PCT Search Report for International Application No. PCT/IL2018/050659 mailed Oct. 8, 2018, 5 pp.
PCT Written Opinion for International Application No. PCT/IL2018/050659 mailed Oct. 8, 2018, 5 pp.
PCT Preliminary Report on Patentability for International Application No. PCT/IL2018/050659, dated Dec. 17, 2019, 6 pp.

* cited by examiner

COMPOSITIONS AND METHODS FOR DETECTION OF GENOMIC VARIATIONS

CROSS REFERENCE TO RELATED APPLICATIONS

This application is a National Phase of PCT Patent Application No. PCT/IL2018/050659 having International filing date of Jun. 14, 2018, which claims the benefit of priority of U.S. Provisional Patent Application No. 62/519,966, filed Jun. 15, 2017, the contents of which are incorporated herein by reference in their entirety.

FIELD OF THE INVENTION

The present invention is directed to compositions and assays useful in genetic variation detection and classification. More specifically, the invention involves a method to enable observation and quantification of uniquely-coded genetic variations by nanopores, circumventing molecular amplification (i.e. PCR).

BACKGROUND OF THE INVENTION

In biomedical research and in medicine in general, a method for the identification and classification of diseases based on genomic material is crucial for a variety of diagnostic applications including antimicrobial-resistant pathogens classification and cancer detection.

A main challenge for genomic based disease identification and characterization stems from the fact that related analytes, such as pathogens genes and cancer biomarkers, are present in extremely low concentrations in biomedical samples. For instance, it is challenging to detect low levels of circulated tumor markers such as KRAS, NRAS, HRAS, BRAF, PIK3CA, p53, or β-catenin in blood, regardless of cancer types (bladder, breast, colorectal, pancreatic, prostate, melanoma, hepatocellular and more). Identification and analysis of these low amounts of markers is crucial for early detection, treatment assessment and determination of cancer recurrence following treatment. Further, it is essential to be able to detect and identify pathogenic bacteria with a small amount of sample. It is widely accepted today that genotyping of antibiotic resistant bacteria can improve survival rate by providing adequate antibiotic treatment.

Currently, most clinical genomic identification approaches are based on PCR (Polymerase Chain Reaction) amplification which introduces high error values to any diagnosis, involves expensive reagents, and generally restricts the level of multiplexity of the test and hence its accuracy. While next-generation sequencing methods allow for whole-genome sequencing, this method requires lengthy sample preparation, often involving amplification as well, and yields much more data than is necessary for accurate classification of DNA and thus requires extensive processing and analysis.

Alternatively, genetic features such as single nucleotide variations (SNVs), insertions and deletions can be used for genotyping. The ligation reaction is a common method used for SNV detection due to its high specificity, low cost, and simplicity. Commonly, samples are designed such that a fluorophore will emit fluorescence only when ligation occurs. However, despite the specificity of ligation, these techniques suffer from low sensitivity due to the low signal to noise ratio (SNR), and limited ability for multiplexing.

Solid state Nanopores (ssNPs) are ultra-sensitive single-molecule biosensors capable of probing extremely low levels of nucleic acids with high accuracy. ssNPs, however, lack the ability to distinguish among individual nucleotides. In nanopore barcoding, a specific sequence is represented by a unique barcode, which is interpreted via electrical or optical signals. Optical sensing, greatly expands the capabilities of nanopores by allowing high specificity and sensitivity detection of a large variety of analytes in the same sample, hence allowing high throughput diagnosis. A method of high throughput, low cost, accurate detection and classification of genomic variation is greatly in need.

SUMMARY OF THE INVENTION

The present invention provides compositions, kits and methods useful for detection and identification of a genomic variant in a sample.

According to a first aspect, there is provided a method for detection of a nucleic acid variant in a sample, comprising:
a. providing a sample containing nucleic acids;
b. contacting the sample with at least one nanopore-sensible barcode linked to nucleic acids complementary to a first sequence, the first sequence comprising a first region of a nucleic acid template adjacent to the variant; and at least one selection marker linked to nucleic acids complementary to a second sequence, the second sequence comprising a second region contiguous to the first sequence in the nucleic acid template, wherein the first or second sequence further comprises the variant at an end of the first or second sequence;
c. contacting the sample with a ligase;
d. isolating a composition containing the selection marker; and
e. passing the composition through at least one nanopore configured to sense the barcode;
thereby detecting a nucleic acid variant in a sample.

According to another aspect, there is provided a composition comprising a nucleic acid template, a nanopore-sensible barcode linked to nucleic acids complementary to a first portion of the nucleic acid template, and a selection marker linked to nucleic acids complementary to a second portion of the nucleic acid template, wherein the first portion and the second portion are contiguous on the nucleic acid template and wherein the nucleic acids complementary to a first portion and the nucleic acids complementary to a second portion are ligated together.

According to another aspect, there is provided a kit comprising:
a. at least one nanopore-sensible barcode;
b. at least one selection marker; and
c. at least one ligase.

According to some embodiments, the nucleic acid template comprises a nucleic acid variant.

According to some embodiments, the nucleic acid variant is selected from the group consisting of: a single nucleotide variation, an insertion, a deletion and a combination thereof.

According to some embodiments, the nucleic acid variant is a genomic variation.

According to some embodiments, the nucleic acid variant is at an end of the first sequence not linked to the barcode or an end of the second sequence not linked to the selection marker and the first and second sequences are contiguous at the variant. According to some embodiments, the nucleic acid variant is at an end of the first portion of the nucleic acid template and is directly ligated to the second portion.

According to some embodiments, the barcode is linked to a 5' end of the nucleic acids and the selection marker is linked to a 3' end of the nucleic acids or the barcode is linked to a 3' end of the nucleic acids and the selection marker is linked to a 5' end of the nucleic acids.

According to some embodiments, the nucleic acids complementary to the first and second sequence or portion comprise any one of: DNA, RNA, PNA, LNA, Morpholino and a combination thereof.

According to some embodiments, the barcode comprises at least one of: a DNA sequence, a fluorophore, and a bulky group. According to some embodiments, the barcode comprises DNA and wherein the DNA is formulated to be hybridized to a molecular beacon. According to some embodiments, the molecular beacon is modified with an amine group, a thiol group, an azide group or biotin. According to some embodiments, the amine group, thiol group, azide group or biotin is labeled with at least one fluorophore, nanoparticle, or nanodiamond. According to some embodiments, the amine group, thiol group, azide group or biotin is labeled with a plurality of fluorophores, nanoparticles or nanodiamonds and the fluorophores, nanoparticles or nanodiamonds are uniquely ordered. According to some embodiments, the nanoparticle is selected from a quantum dot and a gold nanoparticle.

According to some embodiments, the selection marker is selected from the group consisting of: biotin, His, human influenza hemagglutinin (HA), glutathione-S-transferase (GST), chitin binding protein (CBP), maltose binding protein (MBP), Myc, NE and FLAG. According to some embodiments, the selection marker is biotin.

According to some embodiments, a 5' end of the nucleic acids complementary to a first sequence or a second sequence not linked to the barcode or the selection marker contains a 5' phosphorylation.

According to some embodiments, the nanopore is configured for at least one of electrical identification, optical identification, bulky group electrical identification and electro-optical identification.

According to some embodiments, the nucleic acid variant is from a source selected from bacterial genomic DNA, bacterial plasmids, human genomic DNA, viral nucleic acids and RNA. According to some embodiments, the human genomic DNA is from a diseased cell. According to some embodiments, the disease is cancer.

According to some embodiments, the sample is extracted from a cell line, organ biopsy, bodily fluid or an exosome.

According to some embodiments, the sample containing nucleic acids comprises the nucleic acid template comprising the variant, and wherein the barcode, the selection marker, and the nucleic acid template comprising the variant form a single molecule following contact with the ligase.

According to some embodiments, the methods of the invention further comprise disassociating the nanopore-sensible barcode linked to nucleic acids and the selection marker linked to nucleic acids from the temple before the isolating and returning the sample to conditions suitable for hybridization and ligation.

According to some embodiments, the nanopore is a nanopore chip, and the nanopore chip is configured in a solid-state membrane comprising a semiconductor or insulating material. According to some embodiments, the nanopore chip is fabricated in a silicon compound membrane. According to some embodiments, the nanopore chip contains multilayer metallic structures. According to some embodiments, the nanopore is fabricated using any one of: a TEM microscope, a helium ion microscope, and a method of dielectric breakdown.

According to some embodiments, at least one step of the method is performed on a microfluidic device.

According to some embodiments, the methods of the invention are for unique detection of the nucleic acid variants, wherein the variant is within close proximity to at least one other nucleic acid variant. According to some embodiments, the compositions of the invention are for use in the detection or identification of a nucleic acid variant.

According to some embodiments, the kits of the invention are for use in the detection or identification of a nucleic acid variant.

According to some embodiments, the kits of the invention further comprise instructions for use of the kit. According to some embodiments, the kits of the invention comprise a plurality of nanopore-sensible barcodes. According to some embodiments, the kits of the invention comprise a plurality of selection markers.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee

DETAILED DESCRIPTION OF THE INVENTION

Figure 1:
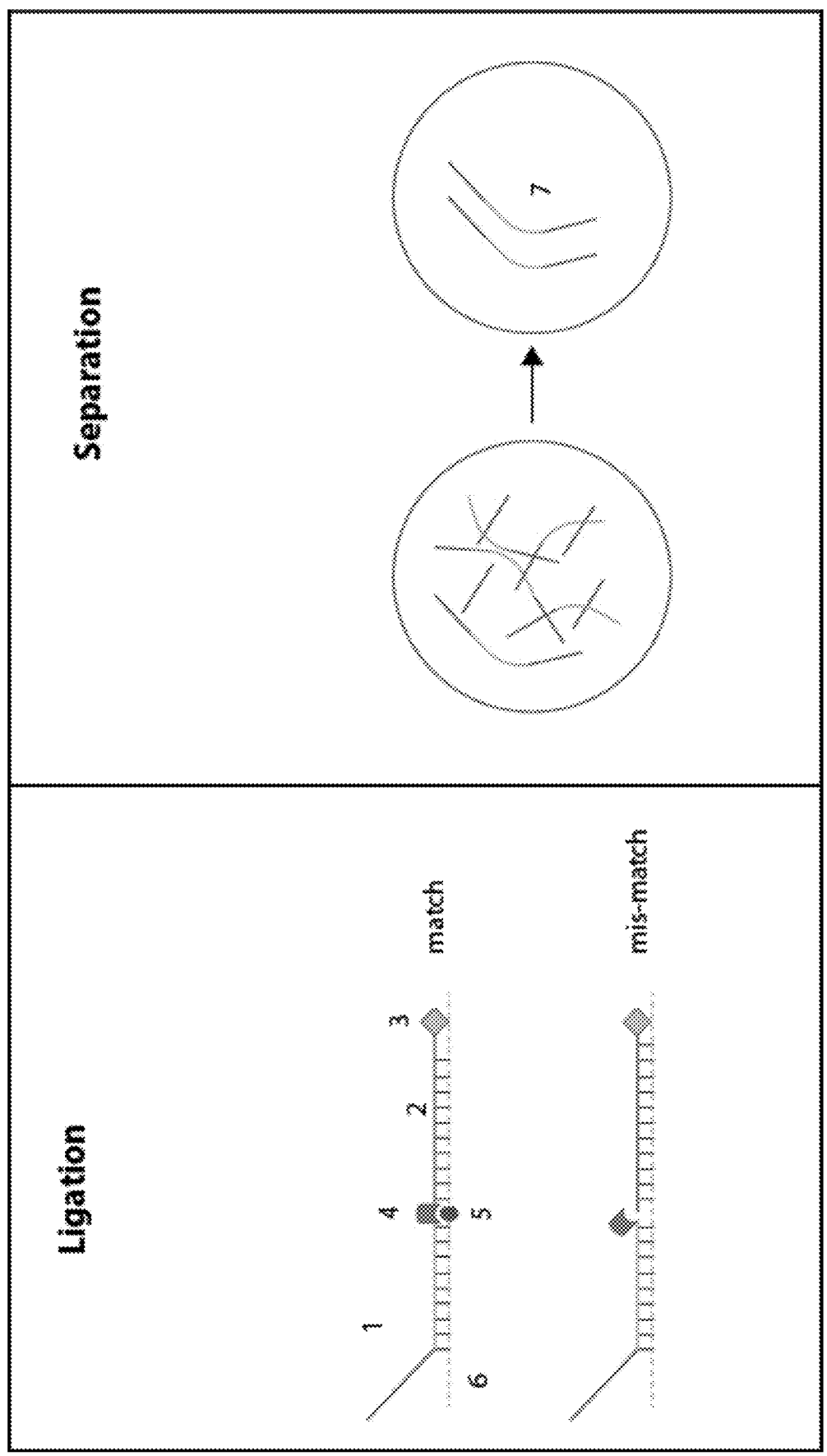
FIG. 1: A schematic illustration of the genetic variation detection assay. Barcode probe (1) contains an ssNP-readable unique tag and selection probe (2), containing an affinity tag (3) are hybridized to the template genomic DNA (6). DNA ligase (4) is then introduced and will ligate the two probes only if the SNV (5) is present. The ligated products ("DNA Nanopore Probes") (7) are separated from the other components in the solution using the affinity tag (3). Nanopore sensing (8) is then used in order to scan the barcode from the ligated product and the sample is classified accordingly. The classification is performed according to either one of at least three possible schemes: by the dwell time of the translocation event (9), a unique blockage signature of the signal (10) or a unique order of colors in case optical detection is used (11).
Figure 1:
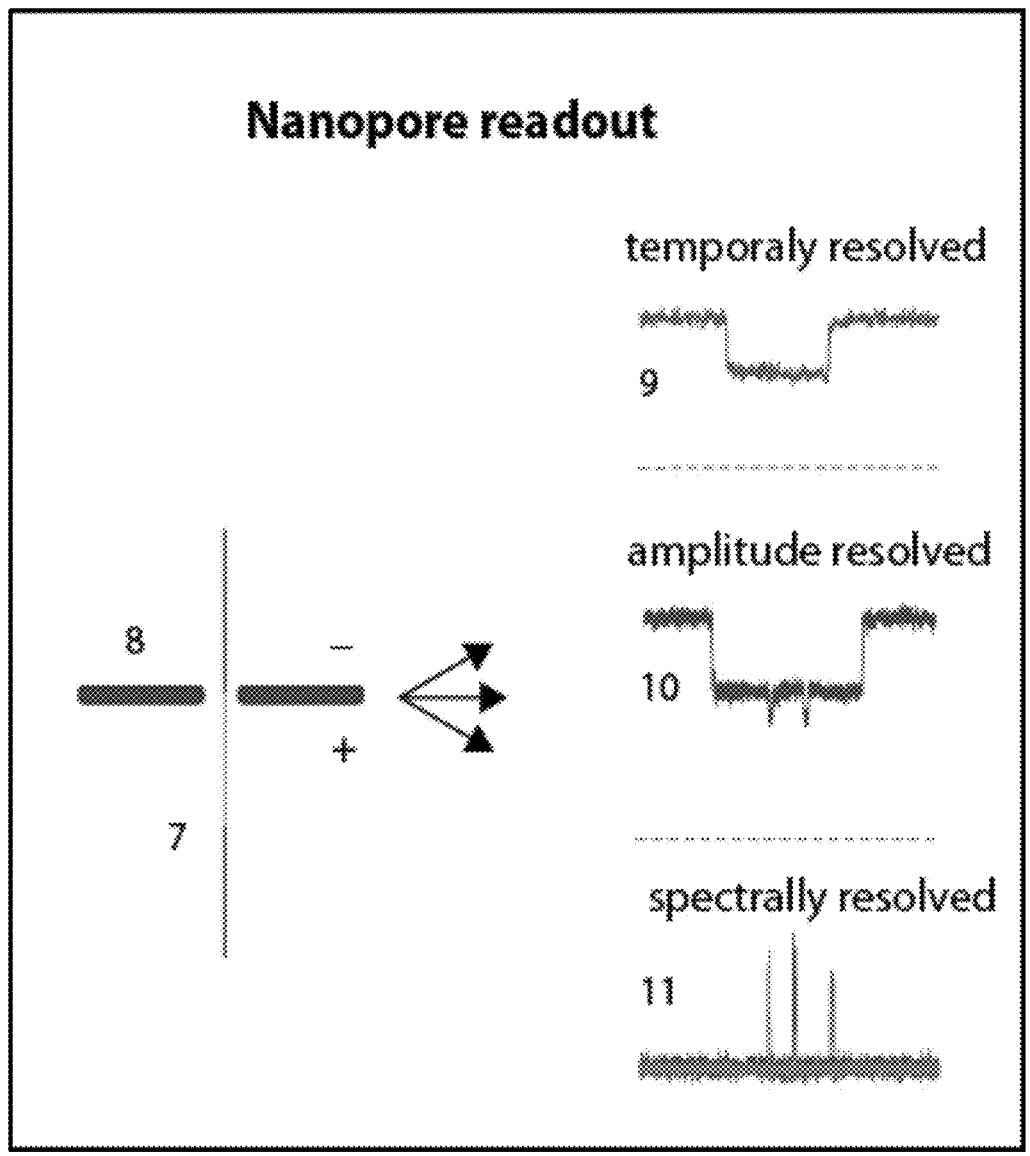

The present invention is a solid state nanopore (ssNP)-based, genotyping technique that circumvents DNA amplification and sequencing, and can provide unprecedented accuracy in identification of genetic variations such as SNVs and insertions/deletions in an extremely short time. The invention involves the creation of an assay to uniquely transform genetic variations to molecular forms that are readily observed by nanopores at the single molecule level. The signal acquired by the nanopore is interpreted as molecularly-encoded barcodes, which allow for unique classification of the source genome with high diagnostic accuracy and high levels of multiplexity.

ssNPs are single-molecule biosensors which can detect and identify a broad range of analytes. These sensors have attracted increasing attention in the past decade due to their extremely high sensitivity and versatility. An electric field applied across a membrane containing a nanometric-scale pore, causes the translocation of charged analytes, which can be observed via blockades in the ionic current flowing through the pore. These blockages have distinct amplitudes and dwell-times which directly correspond to the local cross section and local charge of the biomolecules. However, ssNPs cannot distinguish among individual DNA bases. To enable multiplexed genotyping, which often involves SNVs detection, we describe here a new assay to uniquely encode the SNVs into molecular barcodes that are readily identified by electrical and/or optical means when the molecular barcodes are threaded through a ssNP. These components allow for the development of NP based genotyping assays in which specific genomic information is identified as the molecule translocates through the pore, and the molecule is classified accordingly.

One example of the utility of this method is the quick, accurate diagnosis of which pathogen strain is affecting patients with bacterial infections. A second example is the detection of early-stage cancers from circulated tumor DNA (ctDNA). A main advantage of this invention is that it allows for multiplexed detection of multiple genomic templates with variations present in a sample.

This DNA barcode formation method utilizes a sequence-specific ligation reaction using a set of probes designed to target specific sequences in the genome. Following a purification step, the DNA ligation products are analyzed using the ssNP sensor, using either pure electrical signal detection, pure optical signal sensing or both. Following minimal data processing, a barcode readout classifies the sample analyzed.

By one aspect the present invention provides a method for detection of a genomic variant in a sample, comprising:
a. providing a sample containing nucleic acids;
b. contacting said sample with at least one nanopore-sensible barcode linked to nucleic acids complementary to a first portion of said genomic variant; and at least one selection marker linked to nucleic acids complementary to a second portion of said genomic variant, wherein said first portion and said second portion are contiguous in said genomic variant;
c. contacting said sample with a ligase;
d. isolating a composition containing said selection marker; and
e. passing said composition through at least one nanopore; thereby detecting a genomic variant in a sample.

By another aspect, the present invention provides a method for detection of a nucleic acid variant in a sample, comprising:
a. providing a sample containing nucleic acids;
b. contacting the sample with at least one nanopore-sensible barcode linked to nucleic acids complementary to a first sequence, the first sequence comprising a region adjacent to the variant; and at least one selection marker linked to nucleic acids complementary to a second sequence, the second sequence comprising a region contiguous to the first sequence, wherein the first or second sequence further comprises the variant;
c. contacting the sample with a ligase;
d. isolating a composition containing the selection marker; and
e. passing the composition through at least one nanopore configured to sense the barcode;
thereby detecting a nucleic acid variant in a sample.

By another aspect, the present invention provided a method for detection of a nucleic acid variant in a sample, comprising:
a. providing a sample containing nucleic acids;
b. contacting the sample with at least one nanopore-sensible barcode linked to nucleic acids complementary to a first sequence, the first sequence comprising a first region of a nucleic acid template adjacent to the variant; and at least one selection marker linked to nucleic acids complementary to a second sequence, the second sequence comprising a second region contiguous to the first sequence in the nucleic acid template, wherein the first or second sequence further comprises the variant at an end of the first or second sequence;
c. contacting the sample with a ligase;
d. isolating a composition containing the selection marker; and
e. passing the composition through at least one nanopore configured to sense the barcode;
thereby detecting a nucleic acid variant in a sample.

By another aspect, the present invention provides a composition comprising a nucleic acid template, a nanopore-sensible barcode linked to nucleic acids complementary to a first portion of said nucleic acid template, and a selection marker linked to nucleic acids complementary to a second portion of said nucleic acid template, wherein said first portion and said second portion are contiguous on said nucleic acid template and wherein said nucleic acids complementary to a first portion and said nucleic acids complementary to a second portion are ligated together.

By another aspect, there is provided a kit comprising:
a. at least one nanopore-sensible barcode;
b. at least one selection marker; and
c. at least one ligase.

In some embodiments of the compositions of the invention, the nucleic acid template comprises a genomic variant. In some embodiments, the composition is for use in the detection or identification of a genomic variant. As used herein, the term "template" or "nucleic acid template" are used synonymously and refer to a nucleic acid molecule that comprises the variant and to which the various probes hybridize due to complementarity.

In some embodiments, the nucleic acid variant is a genomic variant. In some embodiments, the nucleic acid variant is a variant RNA transcribed from a genomic variant. In some embodiments, the variant RNA is selected from a variant mRNA, and a variant noncoding RNA. In some embodiments, the variant noncoding RNA is selected from a variant lncRNA, and a variant microRNA. As used herein, the terms "genomic variant", "genetic variant", "nucleic acid variant" and "variant" are used interchangeably and refer to any nucleotide sequence which can be used to identify a specific genome. In some embodiments, the genomic variant is selected from the group consisting of: a single nucleotide variation (SNV), an insertion, a deletion and a combination thereof. In some embodiments, the genomic variant is a SNV. Such genetic variants will be well known to those skilled in the art, and variants unique to specific cancers, tumors, viruses or bacterial strains are well known. Identification of the variant comprises identification of the unique change in a nucleotide that is different from a wild-type or consensus sequence. In some embodiments, the variant is a mutation.

It will be understood by one of skill in the art, that the variants chosen to be probed will be selected based on the specific disease, or organism being detected. In some embodiments, one variant is probed for. In some embodiments, a plurality of variants is probed for. In some embodiments, at least 1, 2, 3, 4, 5, or 10 variants are probed for. Each possibility represents a separate embodiment of the invention. In some embodiments, one variant is detected. In some embodiments, a plurality of variants is detected. In some embodiments, at least 1, 2, 3, 4, 5 or 10 variants are detected. Each possibility represents a separate embodiment of the invention. In some embodiments, the variant is in close proximity to at least one other nucleic acid variant. It will be understood by one skilled in the art that when two variations are close to each other in the genome it can be difficult to detect both. It also may be difficult to detect either as the presence of a second variation may detract from binding or recognition. An unexpected benefit of the current method is that variations in close proximity can still be individually detected, and also can be detected together. This allows for multiplexed detection of even very closely related mutations.

In some embodiments, close proximity comprises a distance of at most 0, 1, 2, 3, 4, 5, 6, 7, 8, 9, 10, 15 or 20 bases between variants. Each possibility represents a separate embodiment of the invention. In some embodiments, close proximity comprises a distance of between 0-20, 0-15, 0-10, 0-7, 0-5, 0-3, 1-20, 1-15, 1-10, 1-7, 1-5, 1-3, 2-20, 2-15, 2-10, 2-7, 2-5, 2-3, 3-20, 3-15, 3-10, 3-7, or 3-5 bases between the variants. Each possibility represents a separate embodiment of the invention. In some embodiments, close proximity is not adjacent. In some embodiments, the other variant is not adjacent to the first variant. In some embodiments, close proximity is at most 3 bases between variants. In some embodiments, close proximity is at least 3 bases between variants. In some embodiments, close proximity is between 3 and 10 bases between variants.

In some embodiments, the genomic variant is from a source selected from bacterial genomic DNA, bacterial plasmids, human genomic DNA, and viral nucleic acids. In some embodiments, the genomic variant is from a source selected from bacterial genomic DNA, bacterial plasmids, human genomic DNA, viral nucleic acids and RNA. In some embodiments, the virus is a DNA virus. In some embodiments, the virus is an RNA virus. In some embodiments, the human genomic DNA is from a diseased cell. In some embodiments, the disease is cancer. In some embodiments, the genomic variant is a driver mutation in the cancer. In some embodiments, the DNA is from a fetus. In some embodiments, the DNA is from cell free DNA (cfDNA). In some embodiments, the DNA is from cell free fetal DNA (cffDNA). In some embodiments, the DNA is from amniocenteses.

In some embodiments, the first portion of the genomic variant is the first sequence. In some embodiments, the first portion comprises the variant. In some embodiments, the first portion of the genomic variant is a sequence adjacent to the variant and including the variant. In some embodiments, the variant is at an end of the first portion or the first sequence. In some embodiments, the end is not the end linked to the barcode.

In some embodiments, the second portion of the genomic variant is the second sequence. In some embodiments, the second portion comprises a region contiguous to the first sequence. In some embodiments, the second portion or second sequence is adjacent to the variant. In some embodiments, the second portion or sequence comprises the variant. In some embodiments, the second portion or sequence does not comprise the variant. In some embodiments, the second portion or sequence is adjacent to the variant and does not comprise sequence from the first portion or sequence. In some embodiments, the second portion or sequence is contiguous with the variant. In some embodiments, an end of the second portion or sequence is directly adjacent to the variant. In some embodiments, the end is not the end linked to the selection marker.

In some embodiments, the variant is at an end of the first sequence or portion not linked to the barcode. In some embodiments, the variant is at an end of the second sequence or portion not linked to the selection marker. In some embodiments, the variant is at an end of the first or second sequence or portion, wherein that end is not linked to the barcode or selection marker. In some embodiments, the first and second sequences or portion are contiguous at the variant. That is the point of continuity between the first and second sequences/portions is the variant. In some embodiments, the variant is at the site of ligation. In some embodiments, the variant is on either side of the ligation site. In some embodiments, the end of the second sequence or portion not linked to the selection marker is contiguous with the variant. In some embodiments, the end of the first sequence or portion not linked to the barcode is contiguous with the variant.

In some embodiments, the nucleic acids complementary to a first or second sequence or portion comprise any one of DNA, RNA, PNA, LNA, Morpholino and a combination thereof. In some embodiments, the nucleic acids complementary to a first or second sequence or portion comprise any one of DNA, RNA, PNA, LNA, and a combination thereof. In some embodiments, the nucleic acids complementary to a first or second sequence or portion comprise any one of DNA, and RNA. In some embodiments, the barcode linked to nucleic acids is a barcode probe. In some embodiments, the selection marker linked to nucleic acids is a selection probe. In some embodiments, the probes are ligated together. In some embodiments, the barcode is linked at the 3' or 5' end of the nucleic acids. In some embodiments, the selection marker is linked at the 3' or 5' end of the nucleic acids. In some embodiments, the barcode is linked at the 5' end and the selection marker is linked at the 3' end or the barcode is linked at the 3' end and the selection marker is linked at the 5' end. In some embodiments, the probe with an unlinked 5' end comprises a 5' phosphate or phosphorylation. In some embodiments, an unlinked 5' end comprises a 5' phosphate or phosphorylation. In some embodiments, all unlinked 5' ends comprise 5' phosphates or phosphorylation.

In some embodiments, the barcode is configured to be read or sensed by a nanopore. In some embodiments, the barcode comprises at least one of: a DNA sequence, a fluorophore, and a bulky group. In some embodiments, the barcode comprises DNA and wherein the DNA is formulated to be hybridized to a molecular beacon. In some embodiments, the molecular beacon is modified with an amine group. In some embodiments, the molecular beacon is modified with a thiol group. In some embodiments, the molecular beacon is modified with an azide group. In some embodiments, the molecular beacon is modified with biotin. In some embodiments, the molecular beacon is modified with an amide group, a thiol group, an azide group or biotin. In some embodiments, the amine group, thiol group, azide group or biotin is labeled with at least one fluorophore. In some embodiments, the amine group, thiol group, azide group or biotin is labeled with at least one nanoparticle. In some embodiments, the amine group, thiol group, azide group or biotin is labeled with at least one nanodiamond. In some embodiments, the amine group, thiol group, azide group or biotin is labeled with at least one fluorophore, nanoparticle or nanodiamond. In some embodiments, the amine group is labeled with a plurality of fluorophores, nanoparticles or nanodiamonds and the fluorophores, nanoparticles or nanodiamonds are uniquely ordered. In some embodiments, the nanoparticle is selected from a quantum dot and a gold nanoparticle.

As used herein, "linked" refers to two molecules being coupled, connected, bound, or in any way physically attached one to the other. Methods of linking barcodes to oligonucleotides are well known in the art. Methods of synthesizing oligonucleotides are also known and several commercial entities can produce custom oligonucleotides, such as IDT DNA, Sigma, and Thermo Fisher.

As used herein, "contiguous" refers to the two portions put together perfectly matching the template sequence such that there is no gap. It will be understood by one of skill in the art, that if a gap exists when the two probes hybridize to the template, or if only one probe hybridizes, the ligase will not ligate the two probes together. In some embodiments, the two portions/probes/sequences are contiguous at the variant. That is the variant is located at the junction of the two contiguous portions.

In some embodiments, the barcode nucleic acid sequence is 5' to the selection nucleic acid sequence. In some embodiments, the barcode nucleic acid sequence is 3' to the selection nucleic acid sequence. In some embodiments, the barcode nucleic acid sequence is 5' or 3' to the selection nucleic acid sequence. In some embodiments, the nucleic acids complementary to a second portion of the genomic variant contains a 5' phosphorylation. In some embodiments, the nucleic acids complementary to a first portion of the genomic variant contains a 5' phosphorylation.

In some embodiments, the sample containing nucleic acids comprises a template nucleic acid molecule comprising the variant, and the barcode, the selection marker, and the template form a single molecule following contact with the ligase. In some embodiments, the barcode, the selection marker and the first and second sequences/portions form a single molecule following contact with the ligase. In some embodiments, the sample comprises a template nucleic acid molecule comprising the variant, and the contacting with a ligase comprises ligation of the first and second sequences/portions. In some embodiments, the composition of the invention comprises a single molecule comprising the barcode, the selection marker and the first and second sequences/portions. In some embodiments, the first and second sequences/portions are contiguous such and the barcode and selection markers are linked at to the ends of the single molecule. In some embodiments, the first and second sequences/portions are linked by ligation. In some embodiments, the first and second sequences/portions are linked such that they comprise a sequence comprising the variant and variant-adjacent nucleic acid sequence. In some embodiments, the first and second sequences/portions are linked such that they comprise a sequence identical to a nucleic acid sequence of the variant. In some embodiments, the first and second sequences/portions are linked such that they consist of a sequence identical to a nucleic acid sequence of the variant.

In some embodiments, sequence adjacent to the variant comprises at least 1, 3, 5, 7, 9, 10, 12, 15, 17 or 20 bases upstream of the variant. Each possibility represents a separate embodiment of the invention. In some embodiments, sequence adjacent to the variant comprises at least 1, 3, 5, 7, 9, 10, 12, 15, 17 or 20 bases downstream of the variant. Each possibility represents a separate embodiment of the invention. In some embodiments, sequence adjacent to the variant comprises at least 1, 3, 5, 7, 9, 10, 12, 15, 17 or 20 bases upstream or downstream of the variant. Each possibility represents a separate embodiment of the invention. In some embodiments, sequence adjacent to the variant comprises at least 1, 3, 5, 7, 9, 10, 12, 15, 17, 20, 25, 30, 35, 40, 45 or 50 bases surrounding of the variant. Each possibility represents a separate embodiment of the invention.

In some embodiments, the contacting of the probes to the sample is performed in conditions suitable for nucleic acid hybridization. Hybridization conditions are well known in the art and can be modified depending on the type of nucleic acid being hybridized, the length of the probes or template, the complexity of the probes or template, the Tm of the probes or template, the GC content of the probes or template or any other characteristic of the hybridization that affects the optimal condition. The hybridization conditions may also be modified to increase or decrease the chance of mismatching between the probe and the template but relaxing the conditions to allow mismatching may lead to increased false positives. Depending on the composition of the sample provided different changes may need to be made to make the sample suitable for hybridization. In some embodiments, the sample is heated to a temperature suitable for hybridization. In some embodiments, the sample is cooled after hybridization to halt further hybridization. In some embodiments, most than one cycle of heating and cooling is performed. In some embodiments, the nucleic acids are isolated or purified from the sample before contacting. In some embodiments, after purification/isolating of the nucleic acids from the sample that are transferred to a buffer suitable for hybridization. In some embodiments, the hybridization conditions and the ligation conditions are the same. In some embodiments, the conditions in the sample are changed after hybridization to facilitate ligation.

In some embodiments, the contacting with a ligase is performed in conditions suitable for ligase activity. In some embodiments, the conditions are suitable for specific ligase activity. A skilled artisan will understand that the temperature and ionic content of the solution must be such that ligation can occur. At temperatures too high or low ligation may not be possible. Further, specific salt contents or the presence of particular ions may be necessary for ligation to proceed. In some embodiments, the temperature or ionic conditions may be altered to halt ligation. In some embodiments, the temperature may be altered to halt ligation.

In some embodiments, the single molecule comprises more than one copy of the genomic variant. In some embodiments, the method further comprises disassociating the single molecule from the template. In some embodiments, the method further comprises disassociating the nanopore-sensible barcode linked to nucleic acids and the selection marker linked to nucleic acids from the template. In some embodiments, the method further comprises disassociating the probes from the template. In some embodiments, the disassociating is performed after contact with a ligase. In some embodiments, the disassociating is performed before the isolating. In some embodiments, the disassociation comprises heating to a temperature sufficient to cause disassociation. In some embodiments, the disassociation comprises contacting the sample with formamide. In some embodiments, the method of the invention further comprises repeating steps c-d before performing step e. In some embodiments, the method of the invention further comprises repeating ligation. In some embodiments, the method of the invention further comprises returning the sample to conditions suitable for hybridization and ligation. In some embodiments, repeating ligation comprises modulating the conditions of the sample to allow for specific ligating activity of the ligase. In some embodiments, repeating ligation comprises modulating the conditions of the sample to allow for hybridization between the probes and template. The altering of conditions may comprise altering the temperature or ionic conditions in the solution such that the ligase is once again active or that hybridization may once again occur or both. In some embodiments, the disassociating does not inactivate the ligase, and repeating ligation comprises returning the solution to conditions suitable for hybridization. A skilled artisan will appreciate that conditions suitable for hybridization are conditions where specific hybridization between complementary nucleic acid sequences occurs. Such conditions are well known in the art, as are conditions for disassociation and conditions for ligation.

In detecting variants that are very close together it may be optimal to repeat the ligation process. If two probes must compete for the same or similar binding sites, repeating the ligation can be beneficial. This repetition may be performed after removing the first composition containing the selection marker, or before any removal of selection marker is performed. Additionally, a second (or third, fourth, etc.) repetition may be done after disassociating the template from the molecule containing the probes. For example, steps a-c may be performed in which a plurality of probes that bind close to each other are added during step b. The first ligation of step c would occur at a temperature that would allow for specific ligase activity. The sample would then be heated, which would disassociate the template and ligated molecule. The sample could then be cooled such that a new round of hybridization and ligation occurs. These heating and cooling steps may be repeated as many times as desired. The method would then continue with step d-e. Alternatively, after disassociation step d may be performed followed by cooling to a temperature that would allow hybridization and ligation to proceed. In such a scenario new selection probes would need to be added.

In some embodiments, the isolating comprises contacting the sample with a binding partner of the selection marker. In some embodiments, the isolating comprises binding of the selection marker. In some embodiments, the isolating is isolation of any molecule comprising the selection marker. In some embodiments, the isolating comprises column purification. In some embodiments, the binding partner of the selection marker is immobilized and the isolated comprises passing the sample over the immobilized binding partner. In some embodiments, the isolating comprises washing of the molecules comprising the selection marker bound to the binding partner. In some embodiments, the washing comprises a high salt wash. Examples of binding partners, and isolation protocols are well known in the art. Examples of possible binding partners include, but are not limited to, streptavidin, FLAG-binding protein, chitin, maltose, and glutathione. In some embodiments, the binding partner is streptavidin.

In some embodiments, the method of the invention further comprises disassociating the selection marker or a molecule comprising the selection marker from its binding partner following isolating. The method of disassociating will depend on the specific selection marker and binding partner employed; such methods are well known in the art. In some embodiments, the disassociation comprises heating, changing the pH, changing the ionic conditions or adding a detergent or solvent to the isolated composition. In some embodiments, the detergent or solvent is formamide. In some embodiments, the disassociation comprises contacting the isolated composition with formamide. In some embodiments, the method of the invention further comprises a buffer exchange to a buffer compatible with nanopore detection. In some embodiments, the molecule comprising the selection marker is transferred to a compatible buffer. Nanopore detection is well known in the art as are buffers suitable for suspension of the analyte.

In some embodiments, the nanopore is a Solid state Nanopores (ssNPs). In some embodiments, the nanopore is a nanopore chip. In some embodiments, the nanopore chip is configured in a solid-state membrane comprising a semiconductor or insulating material. In some embodiments, the nanopore chip is fabricated in a silicon compound membrane. In some embodiments, the nanopore chip contains multi-layer metallic structures. In some embodiments, the nanopore is fabricated using any one of: a TEM microscope, a helium ion microscope, and a method of dielectric breakdown. In some embodiments, the nanopore is fabricated using any one of: a TEM microscope, a helium ion microscope, and a method of dielectric breakdown.

In some embodiments, the nanopore is configured for at least one of electrical identification, optical identification, bulky group electrical identification and electro-optical identification. In some embodiments, the nanopore is configured for electrical identification. In some embodiments, the nanopore is configured for optical identification. In some embodiments, the nanopore is configured for bulky group electrical identification. In some embodiments, the nanopore is configured for electro-optical identification. In some embodiments, the nanopore is configured to sense the barcode.

As used herein, the term "bulky group" refer to side chains on a molecule that hinder at least one of rotation, interaction or movement of the molecule. Bulky groups for nanopore identification are well known in the art.

Selection markers, or tags are well known in the art. In some embodiments, the selection marker is selected from the group consisting of: biotin, His, human influenza hemagglutinin (HA), glutathione-S-transferase (GST), chitin binding protein (CBP), maltose binding protein (MBP), Myc, NE and FLAG. In some embodiments, the selection marker is biotin. Methods of purification or isolation using selection markers are routine in the art. Such methods employ a binding partner of the marker such as streptavidin or FLAG resin. In some embodiments, the selection marker is not a barcode. In some embodiments, the selection marker is not a nucleic acid. In some embodiments, the selection marker does not comprise a nucleic acid. In some embodiments, the selection marker is not DNA or does not comprise DNA. In some embodiments, the selection marker is a protein. Methods of linking proteins and nucleic acids are also well known in the art. In some embodiments, the selection marker is an isolation marker. In some embodiments, the selection marker is not a drug selection marker.

In some embodiments, the ligase is selected from the group consisting of; Taq ligase, 9° N™ ligase and T4 DNA ligase. Conditions for ligation of nucleic acids are well known in the art and specific temperatures, salt concentrations or other ion concentrations can be optimized by routine methods. A skilled artisan can select the optimal ligase and ligation conditions.

In some embodiments, the sample is extracted from a cell line, organ biopsy, bodily fluid or an exosome. In some embodiments, the sample is extracted from bodily fluid or an exosome. In some embodiments, the sample is extracted from a bodily fluid. In some embodiments, the sample is extracted from an exosome. In some embodiments, the sample is extracted from a cell line. In some embodiments, the sample is extracted from an organ biopsy. In some embodiments, the bodily fluid is selected from the group consisting of: blood, lymph, urine, plasma, cerebral spinal fluid and saliva. In some embodiments, the bodily fluid is selected from the group consisting of: blood, lymph, urine, plasma, cerebral spinal fluid, saliva and amniotic fluid. In some embodiments, the bodily fluid is blood.

In some embodiments, at least one step of the methods of the invention is performed on a microfluidic device.

In some embodiments, the kit further comprises instructions for use of the kit. In some embodiments, the kit is for use in the detection or identification or genomic variants. In some embodiments, the kit is for use in the detection or identification or nucleic acid variants. In some embodiments, the kit is for detection of more than one variant. In some embodiments, the kit is for multiplex detection of a plurality of variants. In some embodiments, the variants are very close or in proximity to each other. In some embodiments, the kit comprises a plurality of nanopore-sensible barcodes. In some embodiments, the kit comprises a plurality of selection markers.

As used herein, the term "about" when combined with a value refers to plus and minus 10% of the reference value. For example, a length of about 1000 nanometers (nm) refers to a length of 1000 nm+−100 nm.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Various embodiments and aspects of the present invention as delineated hereinabove and as claimed in the claims section below find experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Strategies for Protein Purification and Characterization—A Laboratory Course Manual" CSHL Press (1996); all of which are incorporated by reference. Other general references are provided throughout this document.

Herein is described a basic flow of an assay for the identification and classification of single nucleotide mutation or SNVs (FIG. 1). The assay consists of four main components:
  i. Barcode probes
  ii. Selection probes
  iii. Nucleic Acid template (DNA or RNA), can be double stranded or single stranded.
  iv. Ligase Example 1: Probes Design Based on the sequence information available in the public databases, sets of barcode probes (1) and selection probes (2) (DNA oligonucleotides) are designed, each set targeting a specific sequence in the genome which includes a genomic variation. The probes are designed to have a low likelihood of forming stable secondary structures. The barcode probes and selection probes are designed to have similar melting temperatures.

There are two important functions of the barcode probe: (a) it hybridizes specifically to its target genomic sequence, and (b) it contains an ssNP-readable unique tag. The unique tags can be realized in several different ways including: (a) DNA sequences designed to be hybridized to molecular beacons for electrical or optical ssNPs identification. (b) DNA sequences that contain a unique arrangement of fluorophores (for optical readout) or bulky groups (for electrical readout). The sequence of the readable tags as well as the sequence of the molecular beacons are designed to be unique, and to have a low likelihood of formation of stable secondary structures.

For optical readouts the labeling process and subsequent purification are optimized to allow high labeling efficiency for precise barcode classification. Different probes result in different labeling efficiencies.

The selection probes are single-stranded DNA oligos designed to have matching sequence to their target genomic sequence (6), and a purification tag (3) (such as biotin) to facilitate a downstream separation process.

Based on sequence information available in public databases, the minimal probe set required is designed for discrimination between chosen prototypical pathogens. This generally involves the placement of the discriminating nucleotides at the 3' end of the barcode probes. In this set up a mismatch that would occur between a WT sequence and a variation-specific primer would be directly adjacent to the selection probe. A mismatch at the ligation site, results in almost no ligation and thus a very low false positive rate.

Example 2: Ligation of Barcode Probe and Selection Probe on the Template

A ligation based single nucleotide substitution detection is known as an assay for detecting the presence of a specific DNA sequence. In this technique, two ligation probes are hybridized to denatured DNA template such that the 5' end of the first probe is adjacent to the 3' end of the second probe. DNA ligase (4) is then introduced, and catalyzes the formation of a phosphodiester bond between the two probes. The method utilizes the well-known high selectivity of the ligation reaction. Namely, ligation does not occur unless there is a full complementarity between the hybridized oligos to the target sequence. This technique was proven to be highly accurate and specific.

Sequence-specific ligation is used in conjunction with a library containing multiple barcode and selection probe pairs to create single stranded DNA Nanopore Probes ("DNPs") (7), but only if the specific SNV (5) is present. For the ligation process, the sheared genomic DNA ("template") (6) will be mixed with the library probes described above and the DNA will be denatured by heating to 94° C. prior to adding the thermo-stable ligase enzyme (4). The ligation itself will be performed at ~60° C. The reaction will then be stopped by cooling. Optimization of the ligation process and the reagents used, results in a high-specificity and high-efficiency reaction which can target a single SNV as well as several nearby (proximity of less than 5 bases) SNVs.

Example 3: DNP Selection

Following ligation, streptavidin-coated magnetic beads (or any other form of affinity purification method) can be used to capture only the fully formed DNPs, and wash away the remainder of the sample (any excess barcode probes and nucleic acids). The DNPs are then released from the beads and directly analyzed by the ssNPs (8).

Example 4: Nanopore Analysis and Barcode Sensing

DNPs can take several forms, to best suit the target application. For example, in applications requiring a high degree of multiplexibility where >10 different SNVs are detected simultaneously the DNPs' barcodes will be realized by a sequence of fluorescent tags that are either directly attached to the barcode probe, or attached via hybridization to molecular beacons.

The DNP is electrophoretically threaded through a nanopore (8) for reading of the barcode. The readout of the barcode probe can be performed in many ways, several examples are detailed here: (a) pure electrical sensing (9); (b) pure optical sensing (11); (c) bulky groups electrical sensing (10); and (d) electro-optical sensing.

A unique arrangement of complementary oligonucleotide sequences on the tag region leads to a distinct readout in the nanopore, based on unique dwell-times. The nanopore is designed to bear a diameter that allows only one strand to translocate through it, which results in unzipping of the oligonucleotides one at a time. The stripping process slows down the translocation speed of the DNP to approximately a few milliseconds per unzipping event and the DNP is classified according to the translocation time which correlates to the number of hybridized oligonucleotides.

The amplitude resolved nanopore measurement (10) consists of a DNA strand that contains a unique arrangement of bulky groups (for electrical readout). This leads to a distinct readout in the nanopore, based on unique translocation amplitudes.

The synchronous electro-optical nanopore measurement (11) involves the hybridized of the DNP with color-coded molecular beacons. Each molecular beacon contains a quencher on its 3' end and a specific fluorophore on its 5' end. Lying at the very heart of the method is the idea that careful design of the barcode probes creates a geometry such that when all the molecular beacons are hybridized to the probe molecules their fluorescence is quenched by a head-to-tail arrangement of the fluorophores and quenchers. The pores will be illuminated with lasers of three different colors and optically monitored. When the DNP enters the pore, the marked beacons are stripped off one at a time, creating a distinct burst of fluorescence. Each released beacon is automatically closed, quenching its own fluorescence while diffusing away from the vicinity of the pore. The DNP is classified according to the sequence of the photon bursts at certain colors throughout the dwell-time of an event as determined by the electrical signal.

In cases where the optical readout involves single fluorophore detection, the electro-optical apparatus as well as the nanopore chip are designed accordingly. Namely, the nanopore chip allows accurate focusing of the lasers on the nanopore itself, with low optical background from molecules diffusing into the detection volume. The optical setup is precisely aligned so that most of the emitted photons from the translocating molecule are collected by the ultra-sensitive detectors.

Finally, a data analysis code allows real time analysis of the obtained data and classification of the barcode profile of each sample. It will calculate the identity of the barcode and assign it a certainty factor based on the data quality. In this way, a bias-free, unmanned pathogen serotyping procedure is achieved.

Example 5: Identifying Single Variations in Different Bacterial Strains

Figure 2:
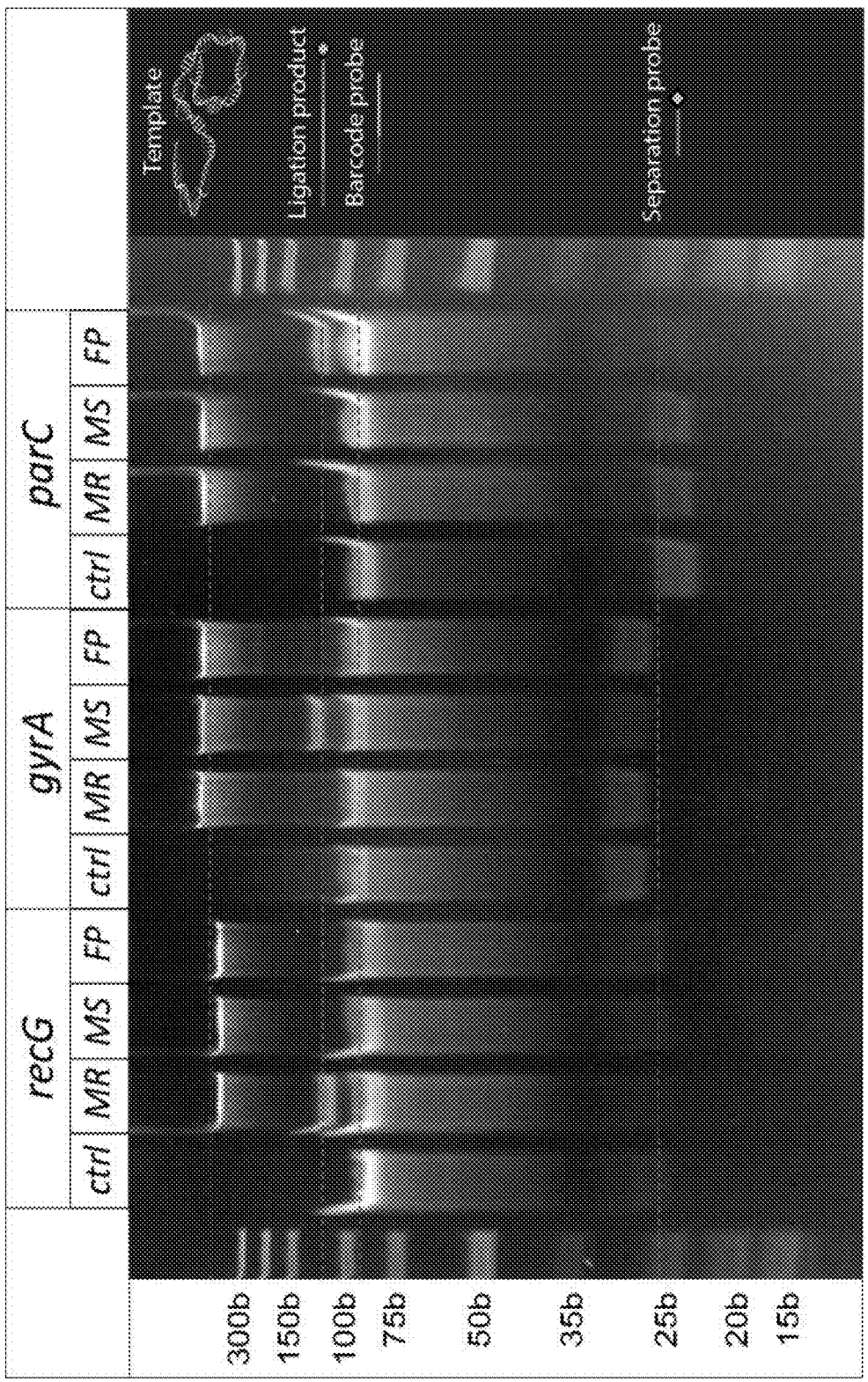
FIG. 2: A photograph of an SDS-PAGE gel showing ligation reactions performed for three genes (recG, gyrA and parC) for three strains (MR, MS and FP). A control, which does not contain template DNA is performed for each gene (lanes 1, 5 and 9). Only one reaction for each gene forms a ligation product (DNP) which is approximately 120 bases long (band labeled ligation product, lanes 2, 7, and 12).

To validate the specificity of the optimized ligation reaction, DNA sequences containing genetic variations were extracted via PCR from the genomic DNA of three bacterial strains: Methicillin susceptible (MS), Methicillin Resistant (MR) and Multi-drug resistant (FP) Staphylococcus Aureus. Sections of three target genes (recG, gyrA and parC) were isolated from each strain and have lengths of ~520 bp, ~940 bp and ~885 bp, respectively. The sequences of each PCR product are provided in Table 1, and the primers used for their amplification are provided in Table 2. In order to assess specificity, a ligation reaction was performed for each strain of all three genes. The same ligation probes (See Table 3) were added for all reactions for the same gene, the only difference being the template DNA used. A 20% PAGE denaturing gel was run of the samples from all of the ligation reactions. Samples were prepared with a loading dye containing formamide and heated to 95° C. for 10 minutes prior to loading. The gel was run at a temperature of 40° C. These heating steps are to ensure adequate denaturation of the samples. As expected, only when there was exact complementarity between the probes and the template DNA, did a DNP form (FIG. 2). That is, variant-specific PCR using the primers provided in Table 3 yielded a labeled ligation product only in the strains baring the genetic variation (lanes 2, 7, and 12 of FIG. 2). This demonstrates that the method of the invention is an effective way to PCR for rare genetic variation that can then be detected and quantified via nanopore technology.

TABLE 1

Sequences of PCR fragments of the *Staphylococcus Aureus* strains (MR, MS, FP) genes: gyrA, parC and recG

| Gene | *Staphylococcus Aureus* strains | Sequence (5'---3') |
| --- | --- | --- |
| gyrA | MR | TTGAAGGAGGAACTCTTGATGGCTGAATTACCTCAATC AAGAATAAATGAACGAAATATTACCAGTGAAATGCGT GAATCATTTTTAGATTATGCGATGAGTGTTATCGTTGCT CGTGCATTGCCAGATGTTCGTGACGGTTTAAAACCAGT ACATCGTCGTATACTATATGGATTAAATGAACAAGGTA TGACACCGGATAAATCATATAAAAAATCAGCACGTAT CGTTGGTGACGTAATGGGTAAATATCACCCTCATGGTG ACTCATCTATTTATGAAGCAATGGTACGTATGGCTCAA GATTTCAGTTATCGTTATCCGCTTGTTGATGGCCAAGG TAACTTTGGTTCAATGGATGGAGATGGCGCAGCAGCA ATGCGTTATACTGAAGCGCGTATGACTAAAATCACACT TGAACTGTTACGTGATATTAATAAAGATACAATAGATT TTATCGATAACTATGATGGTAATGAAAGAGAGCCGTCA GTCTTACCTGCTCGATTCCCTAACTTATTAGCCAATGGT GCATCAGGTATCGCGGTAGGTATGGCAACGAATATTCC ACCACATAACTTAACAGAATTAATCAATGGTGTACTTA GCTTAAGTAAGAACCCTGATATTTCAATTGCTGAGTTA ATGGAGGATATTGAAGGTCCTGATTTCCCAACTGCTGG ACTTATTTTAGGTAAGAGTGGTATTAGACGTGCATATG AAACAGGTCGTGGTTCAATTCAAATGCGTTCTCGTGCA GTTATTGAAGAACGTGGAGGCGGACGTCAACGTATTGT TGTCACTGAAATTCCTTTCCAAGTGAATAAGGCTCGTA TGATTGAAAAAATTGCAGAGCTCGTTCGTGACAAGAA AATTGACGGTATCACTGATTTACGTGATGAAACAAGTT TACGTACTGGTGTGCGTGTCGTTATTGATG (SEQ ID NO: 1) |
|  | FP | TTGAAGGAGGAACTCTTGATGGCTGAATTACCTCAATC AAGAATAAATGAACGAAATATTACCAGTGAAATGCGT GAATCATTTTTAGATTATGCGATGAGTGTTATCGTTGCT CGTGCATTGCCAGATGTTCGTGACGGTTTAAAACCAGT ACATCGTCGTATACTATATGGATTAAATGAACAAGGTA TGACACCGGATAAATCATATAAAAAATCAGCACGTAT CGTTGGTGACGTAATGGGTAAATATCACCCTCATGGTG ACTTATCTATTTATGAAGCAATGGTACGTATGGCTCAA GATTTCAGTTATCGTTATCCGCTTGTTGATGGCCAAGG TAACTTTGGTTCAATGGATGGAGATGGCGCAGCAGCA ATGCGTTATACTGAAGCGCGTATGACTAAAATCACACT TGAACTGTTACGTGATATTAATAAAGATACAATAGATT TTATCGATAACTATGATGGTAATGAAAGAGAGCCGTCA GTCTTACCTGCTCGATTCCCTAACTTATTAGCCAATGGT GCATCAGGTATCGCGGTAGGTATGGCAACGAATATTCC ACCACATAACTTAACAGAATTAATCAATGGTGTACTTA |

TABLE 1-continued

Sequences of PCR fragments of the *Staphylococcus Aureus* strains (MR, MS, FP) genes: gyrA, parC and recG

| Gene | *Staphylococcus* Aureus strains | Sequence (5'---3') |
|---|---|---|
| | | GCTTAAGTAAGAACCCTGATATTTCAATTGCTGAGTTA<br>ATGGAGGATATTGAAGGTCCTGATTTCCCAACTGCTGG<br>ACTTATTTTAGGTAAGAGTGGTATTAGACGTGCATATG<br>AAACAGGTCGTGGTTCAATTCAAATGCGTTCTCGTGCA<br>GTTATTGAAGAACGTGGAGGCGGACGTCAACGTATTGT<br>TGTCACTGAAATTCCTTTCCAAGTGAATAAGGCTCGTA<br>TGATTGAAAAAATTGCAGAGCTCGTTCGTGACAAGAA<br>AATTGACGGTATCACTGATTTACGTGATGAAACAAGTT<br>TACGTACTGGTGTGCGTGTCGTTATTGATG (SEQ ID NO: 2) |
| | MS | TTGAAGGAGGAACTCTTGATGGCTGAATTACCTCAATC<br>AAGAATAAATGAACGAAATATTACCAGTGAAATGCGT<br>GAATCATTTTTAGATTATGCGATGAGTGTTATCGTTGCT<br>CGTGCATTGCCAGATGTTCGTGACGGTTTAAAACCAGT<br>ACATCGTCGTATACTATATGGATTAAATGAACAAGGTA<br>TGACACCGGATAAATCATATAAAAAATCAGCACGTAT<br>CGTTGGTGACGTAATGGGTAAATATCACCCTCATGGTG<br>ACTCATCTATTTATGAAGCAATGGTACGTATGGCTCAA<br>GATTTCAGTTATCGTTATCCGCTTGTTGATGGCCAAGG<br>TAACTTTGGTTCAATGGATGGAGATGGCGCAGCAGCA<br>ATGCGTTATACTGAAGCGCGTATGACTAAAATCACACT<br>TGAACTGTTACGTGATATTAATAAAGATACAATAGATT<br>TTATCGATAACTATGATGGTAATGAAAGAGAGCCGTCA<br>GTCTTACCTGCTCGATTCCCTAACTTATTAGCCAATGGT<br>GCATCAGGTATCGCGGTAGGTATGGCAACGAATATTCC<br>ACCACATAACTTAACAGAATTAATCAATGGTGTACTTA<br>GCTTAAGTAAGAACCCTGATATTTCAATTGCTGAGTTA<br>ATGGAGGATATTGAAGGTCCTGATTTCCCAACTGCTGG<br>ACTTATTTTAGGTAAGAGTGGTATTATTAGACGTGCAT<br>ATGAAACAGGTCGTGGTTCAATTCAAATGCGTTCTCGT<br>GCAGTTATTGAAGAACGTGGAGGCGGACGTCAACGTA<br>TTGTTGTCACTGAAATTCCTTTCCAAGTGAATAAGGCT<br>CGTATGATTGAAAAAATTGCAGAGCTCGTTCGTGACAA<br>GAAAATTGACGGTATCACTGATTTACGTGATGAAACAA<br>GTTTACGTACTGGTGTGCGTGTCGTTATTGATG (SEQ ID NO: 3) |
| parC | MR | GATGAGGAGGAAATCTAGTGAGTGAAATAATTCAAGA<br>TTTATCACTTGAAGATGTTTTAGGTGATCGCTTTGGAA<br>GATATAGTAAATATATTATTCAAGAGCGTGCATTGCCA<br>GATGTTCGTGATGGTTTAAAACCAGTACAACGTCGTAT<br>TTTATATGCAATGTATTCAAGTGGTAATACACACGATA<br>AAAATTTCCGTAAAAGTGCGAAAACAGTCGGTGATGTT<br>ATTGGTCAATATCATCCACATGGAGACTCCTCAGTGTA<br>CGAAGCAATGGTCCGTTTAAGTCAAGACTGGAAGTTAC<br>GACATGTCTTAATAGAAATGCATGGTAATAATGGTAGT<br>ATCGATAATGATCCGCCAGCGGCAATGCGTTACACTGA<br>AGCTAAGTTAAGCTTACTAGCTGAAGAGTTATTACGTG<br>ATATTAATAAAGAGACAGTTTCTTTCATTCCAAACTAT<br>GATGATACGACACTCGAACCAATGGTATTGCCATCAAG<br>ATTTCCTAACTTACTAGTGAATGGTTCTACAGGTATAT<br>CTGCAGGTTACGCGACAGATATACCACCACATAATTTA<br>GCTGAAGTGATTCAAGCAACACTTAAATATATTGATAA<br>TCCGGATATTACAGTCAATCAATTAATGAAATATATTA<br>AAGGTCCTGATTTTCCAACTGGTGGTATTATTCAAGGT<br>ATTGATGGTATTAAAAAAGCTTATGAATCAGGTAAAG<br>GTAGAATTATAGTTCGTTCTAAAGTTGAAGAAGAAACT<br>TTACGCAATGGACGTAAACAGTTAATTATTACTGAAAT<br>TCCATATGAAGTGAACAAAAGTAGCTTAGTAAAACGT<br>ATCGATGAATTACGTGCTGACAAAAAAGTCGATGGTAT<br>CGTTGAAGTACGTG (SEQ ID NO: 4) |
| | FP | GATGAGGAGGAAATCTAGTGAGTGAAATAATTCAAGA<br>TTTATCACTTGAAGATGTTTTAGGTGATCGCTTTGGAA<br>GATATAGTAAATATATTATTCAAGAGCGTGCATTGCCA<br>GATGTTCGTGATGGTTTAAAACCAGTACAACGTCGTAT<br>TTTATATGCAATGTATTCAAGTGGTAATACACACGATA<br>AAAATTTCCGTAAAAGTGCGAAAACAGTCGGTGATGTT<br>ATTGGTCAATATCATCCACATGGAGACTACTCAGTGTA<br>CGAAGCAATGGTCCGTTTAAGTCAAGACTGGAAGTTAC<br>GACATGTCTTAATAGAAATGCATGGTAATAATGGTAGT<br>ATCGATAATGATCCGCCAGCGGCAATGCGTTACACTGA<br>AGCTAAGTTAAGCTTACTAGCTGAAGAGTTATTACGTG<br>ATATTAATAAAGAGACAGTTTCTTTCATTCCAAACTAT<br>GATGATACGACACTCGAACCAATGGTATTGCCATCAAG<br>ATTTCCTAACTTACTAGTGAATGGTTCTACAGGTATAT<br>CTGCAGGTTACGCGACAGATATACCACCACATAATTTA |

TABLE 1-continued

Sequences of PCR fragments of the *Staphylococcus Aureus* strains (MR, MS, FP) genes: gyrA, parC and recG

| Gene | *Staphylococcus Aureus* strains | Sequence (5'---3') |
|---|---|---|
| | | GCTGAAGTGATTCAAGCAACACTTAAATATATTGATAA<br>TCCGGATATTACAGTCAATCAATTAATGAAATATATTA<br>AAGGTCCTGATTTTCCAACTGGTGGTATTATTCAAGGT<br>ATTGATGGTATTAAAAAAGCTTATGAATCAGGTAAAG<br>GTAGAATTATAGTTCGTTCTAAAGTTGAAGAAGAAACT<br>TTACGCAATGGACGTAAACAGTTAATTATTACTGAAAT<br>TCCATATGAAGTGAACAAAAGTAGCTTAGTAAAACGT<br>ATCGATGAATTACGTGCTGACAAAAAAGTCGATGGTAT<br>CGTTGAAGTACGTG (SEQ ID NO: 5) |
| | MS | GATGAGGAGGAAATCTAGTGAGTGAAATAATTCAAGA<br>TTTATCACTTGAAGATGTTTTAGGTGATCGCTTTGGAA<br>GATATAGTAAATATATTATTCAAGAGCGTGCATTGCCA<br>GATGTTCGTGATGGTTTAAAACCAGTACAACGTCGTAT<br>TTTATATGCAATGTATTCAAGTGGTAATACACACGATA<br>AAAATTTCCGTAAAAGTGCGAAAACAGTCGGTGATGTT<br>ATTGGTCAATATCATCCACATGGAGACTCCTCAGTGTA<br>CGAAGCAATGGTCCGTTTAAGTCAAGACTGGAAGTTAC<br>GACATGTCTTAATAGAAATGCATGGTAATAATGGTAGT<br>ATCGATAATGATCCGCCAGCGGCAATGCGTTACACTGA<br>AGCTAAGTTAAGCTTACTAGCTGAAGAGTTATTACGTG<br>ATATTAATAAAGAGACAGTTTCTTTCATTCCAAACTAT<br>GATGATACGACACTCGAACCAATGGTATTGCCATCAAG<br>ATTTCCTAACTTACTAGTGAATGGTTCTACAGGTATAT<br>CTGCAGGTTACGCGACAGATATACCACCACATAATTTA<br>GCTGAAGTGATTCAAGCAACACTTAAATATATTGATAA<br>TCCGGATATTACAGTCAATCAATTAATGAAATATATTA<br>AAGGTCCTGATTTTCCAACTGGTGGTATTATTCAAGGT<br>ATTGATGGTATTAAAAAAGCTTATGAATCAGGTAAAG<br>GTAGAATTATAGTTCGTTCTAAAGTTGAAGAAGAAACT<br>TTACGCAATGGACGTAAACAGTTAATTATTACTGAAAT<br>TCCATATGAAGTGAACAAAAGTAGCTTAGTAAAACGT<br>ATCGATGAATTACGTGCTGACAAAAAAGTCGATGGTAT<br>CGTTGAAGTACGTG (SEQ ID NO: 6) |
| recG | MR | CAACAGTATTATGGTGTTTCCCGTGTAGGGTTATTGCA<br>TGGTAAGTTATCTGCCGATGAAAAAGATGAGGTCATGC<br>AAAAGTTTAGTAATCATGAGATAAATGTTTTAGTTTCT<br>ACTACTGTTGTTGAAGTAGGTGTTAATGTACCGAATGC<br>AACTTTTATGATGATTTATGATGCGGATCGCTTTGGATT<br>ATCAACTTTACATCAGTTACGCGGTCGTGTAGGTAGAA<br>GTGACCAGCAAAGTTACTGTGTTTTAATTGCATCCCCT<br>AAAACAGAAACAGGAATTGAAAGAATGACAATTATGA<br>CACAAACAACGGATGGATTTGAATTGAGTGAACGAGA<br>CTTAGAAATGCGTGGTCCTGGAGATTTCTTTGGTGTTA<br>AACAAAGTGGATTGCCAGATTTCTTAGTTGCCAATTTA<br>GTTGAAGGTTATCGTATGTTAGAAGTTGCTCGTGATGA<br>AGCAGCTGAACTTATTCAATCTGGCGTATTCTTTGAAA<br>ATACGTATCAACATTTACGTCATTTTG (SEQ ID NO: 7) |
| | FP | CAACAGTATTATGGTGTTTCCCGTGTAGGGTTATTGCA<br>TGGTAAGTTATCTGCCGATGAAAAAGATGAGGTCATGC<br>AAAAGTTTAGTAATCATGAGATAAATGTTTTAGTTTCT<br>ACTACTGTTGTTGAAGTAGGTGTTAATGTACCGAATGC<br>AACTTTTATGATGATTTATGATGCGGATCGCTTTGGATT<br>ATCAACTTTACATCAGTTACGCGGTCGTGTAGGTAGAA<br>GTGACCAGCAAAGTTACTGTGTTTTAATTGCATCCCCT<br>AAAACAGAAACAGGAATTGAAAGAATGACAATTATGA<br>CACAAACAACGGATGGATTTGAATTGAGTGAACGAGA<br>CTTAGAAATGCGTGGTCCTGGAGATTTCTTTGGTGTTA<br>AACAAAGTGGATTGCCAGATTTCTTAGTTGCCAATTTA<br>GTTGAAGATTATCGTATGTTAGAAGTTGCTCGTGATGA<br>AGCAGCTGAACTTATTCAATCTGGCGTATTCTTTGAAA<br>ATACGTATCAACATTTACGTCATTTTG (SEQ ID NO: 8) |
| | MS | CAACAGTATTATGGTGTTTCCCGTGTAGGGTTATTGCA<br>TGGTAAGTTATCTGCCGATGAAAAAGATGAGGTCATGC<br>AAAAGTTTAGTAATCATGAGATAAATGTTTTAGTTTCT<br>ACTACTGTTGTTGAAGTAGGTGTTAATGTACCGAATGC<br>AACTTTTATGATGATTTATGATGCGGATCGCTTTGGATT<br>ATCAACTTTACATCAGTTACGCGGTCGTGTAGGTAGAA<br>GTGACCAGCAAAGTTACTGTGTTTTAATTGCATCCCCT<br>AAAACAGAAACAGGAATTGAAAGAATGACAATTATGA<br>CACAAACAACGGATGGATTTGAATTGAGTGAACGAGA<br>CTTAGAAATGCGTGGTCCTGGAGATTTCTTTGGTGTTA<br>AACAAAGTGGATTGCCAGATTTCTTAGTTGCCAATTTA<br>GTTGAAGATTATCGTATGTTAGAAGTTGCTCGTGATGA |

TABLE 1-continued

Sequences of PCR fragments of the *Staphylococcus Aureus* strains (MR, MS, FP) genes: gyrA, parC and recG

| Gene | *Staphylococcus Aureus* strains | Sequence (5'---3') |
|---|---|---|
| | | AGCAGCTGAACTTATTCAATCTGGCGTATTCTTTGAAA ATACGTATCAACATTTACGTCATTTTG (SEQ ID NO: 9) |

TABLE 2

Oligos used for producing PCR fragments for gyrA, parC and recG using *Staphylococcus Aureus* strains (MR, MS, FP).

| Gene | Oligo Name | Sequence (5'---3') |
|---|---|---|
| gyrA | gyrA_for | TTGAAGGAGGAACTCTTGATGG (SEQ ID NO: 10) |
| | gyrA_rev | CATCAATAACGACACGCACA (SEQ ID NO: 11) |
| parC | parC_for | GATGAGGAGGAAATCTAGTG (SEQ ID NO: 12) |
| | parC_rev | CACGTACTTCAACGATACCATCG (SEQ ID NO: 13) |
| recG | recG_for | CAACAGTATTATGGTGTTTCCC (SEQ ID NO: 14) |
| | recG_rev | CAAAATGACGTAAATGTTGATACG (SEQ ID NO: 15) |

TABLE 3

Oligos used for specific Ligation Detection Reaction (LDR) for gyrA, parC and recG using *Staphylococcus Aureus* strains (MR, MS, FP).

| Gene | Oligo Name | Sequence (5'---3') (Complementary portion of barcode probes is underlined) |
|---|---|---|
| gyrA | gyrA_barcode | CGTTCGTCACATAACGCCTCACATCACGG AGGGTTCGTCACATAACGGATGCATTAGG TCGCTGGACTTATTTTAGGTAAGAGTGGT AT (SEQ ID NO: 16) |
| | gyrA_selection | Phosphate- TATTAGACGTGCATATGA AACAGGTC (SEQ ID NO: 17)- Biotin |
| parC | parC_barcode | CGACTAGGTACGGTCGCGACTAGGTACGG TCGCGACTAGGTACGGTCGGATGCATTAG GTCGTCAATATCATCCACATGGAGACTC (SEQ ID NO: 18) |
| | parC_selection | Phosphate-CTCAGTGTACGAAGCAATG GTC (SEQ ID NO: 19)- Biotin |
| recG | recG_barcode | CGACTAGGTACGGTCGCGTTCGTCACATA ACGCGTTCGTCACATAACGGATGCATTAG GTCCTTAGTTGCCAATTTAGTTGAAGG (SEQ ID NO: 20) |
| | recG_selection | Phosphate-TTATCGTATGTTAGAAGTT GCTCG (SEQ ID NO: 21)- Biotin |

Example 6: Identifying Multiple Variations in Different Bacterial Strains

Figure 3:
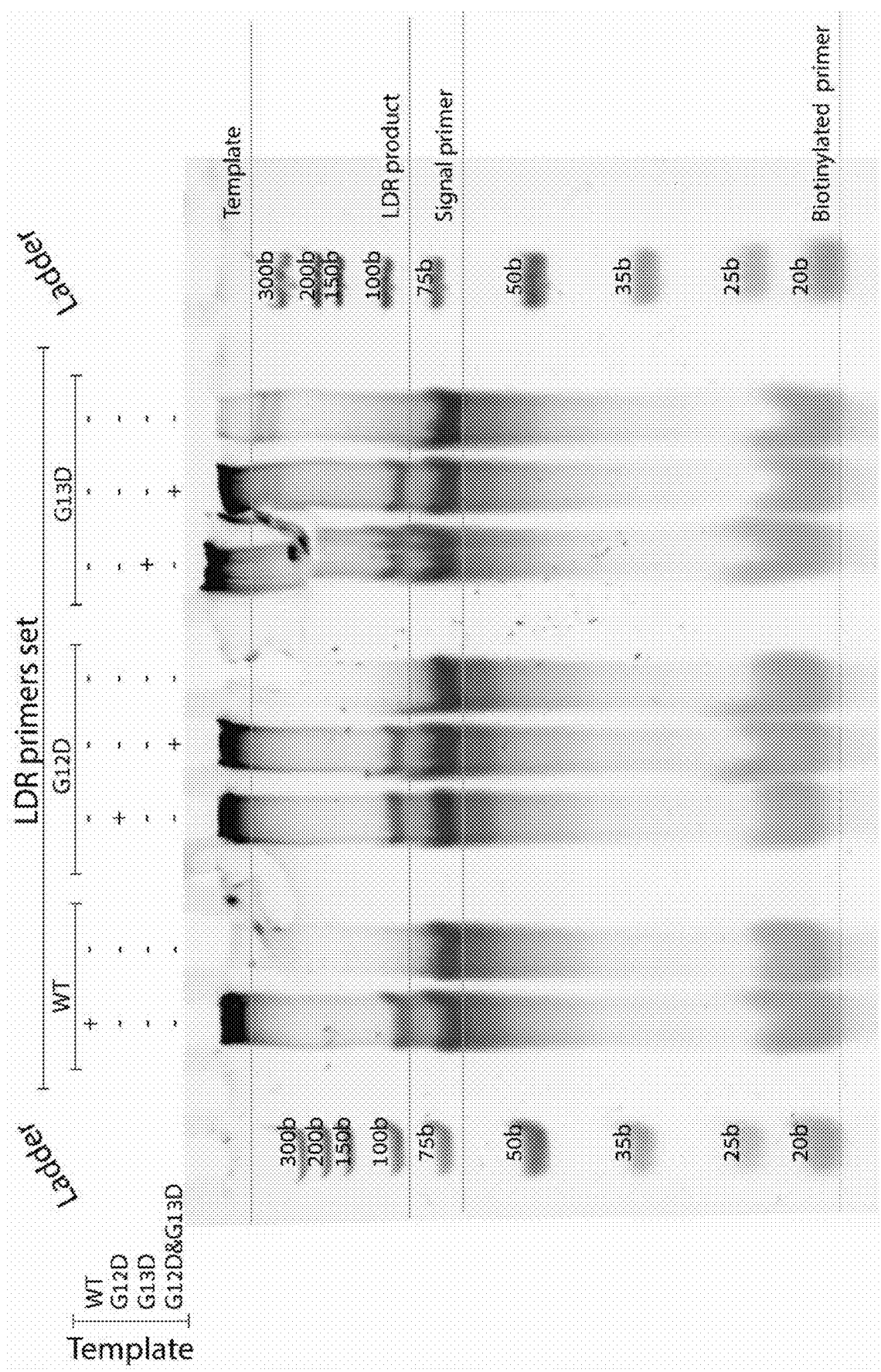
FIG. 3: A photograph of an SDS-PAGE gel showing the ligation detection reaction (LDR) assay for detecting multiple KRAS mutations. The assay has specificity for each type of KRAS mutations with the LDR primers set. The KRAS template with multiple mutations can also be detected using each mutation specific LDR primers set.

Furthermore, validation was performed to demonstrate that the ligation assay can reliably differentiate between normal (WT) and multiple close mutations. The most common KRAS mutations (G12D and G13D) and their combination were chosen for this example (See sequences in Table 4). The two mutations are located close to each other (3 nucleotides apart). However, they possess greatly different prognostic significance, as the KRAS G13D mutation associates with more aggressive cancer and poor survival rates of patients. Therefore, the ability of the assay to specifically differentiate between the two mutations was tested by designing 4 synthetic plasmids which harbor the WT or mutated segment of the KRAS gene that includes the G12D, G13D or both mutations. Two primers, KRAS forward: GGTTTTCCCAGTCACGACG (SEQ ID NO: 26), and KRAS backward: CCAATACGCAAGGAAACAGC (SEQ ID NO: 27) were used to produce 730 bp segments via PCR which were used as templates for the LDR. The ligation primers (Table 5) were designed so the barcode-oligo includes the mutation site at its very 3' end and will be ligated only if there is perfect match at the mutation site. As can be seen in FIG. 3, only when the specific mutated template is present, the ligation occurs. For the combined mutation template, the primers are still able to detect each individual mutation (FIG. 3, lanes 5 and 8).

TABLE 4

Sequences for the amplified PCR fragments (726-730 bp) including the WT KRAS or mutated KRAS exon 2 fragments.

| Synthetic plasmid | Sequence (5'---3') |
|---|---|
| KRAS_WT | GGTTTTCCCAGTCACGACGTTGTAAAACGACGGCCAGT GAGCGCGACGTAATACGACTCACTATAGGGCGAATTGG CGGAAGGCCGTCAAGGCCTAGGCGCGCCATGAGCTCGA TATCGATACACGTCTGCAGTCAACTGGAATTTTCATGA TTGAATTTTGTAAGGTATTTTGAAATAATTTTTCATAT AAAGGTGAGTTTGTATTAAAAGGTACTGGTGGAGTATT TGATAGTGTATTAACCTTATGTGTGACATGTTCTAATA TAGTCACATTTTCATTATTTTTATTATAAGGCCTGCTG AAAATGACTGAATATAAACTTGTGGTAGTTGGAGCTGG TGGCGTAGGCAAGAGTGCCTTGACGATACAGCTAATTC AGAATCATTTTGTGGACGAATATGATCCAACAATAGAG GTAAATCTTGTTTTAATATGCATATTACTGGTGCAGGA CCATTCTTTGATACAGATAAAGGTTTCTCTGACCATTT TCATGAGTACTTATTACAAGATAATTATGCTGAAAGTT AAGTTATCTGAAATGTACCTTGGGTTTCAAGTTATATG TAACCATTAATATGGGAACTTTACTTTCCTTGGGAGAT ATCGGTACCTCTTAATTAACTGGCCTCATGGGCCTTCC GCTCACTGCCCGCTTTCCAGTCGGGAAACCTGTCGTGC CAGCTGCATTAACATGGTCATAGCTGTTTCCTTGCGTA TTGG (SEQ ID NO: 22) |
| KRAS_G12D | GGTTTTCCCAGTCACGACGTTGTAAAACGACGGCCAGT GAGCGCGACGTAATACGACTCACTATAGGGCGAATTGG CGGAAGGCCGTCAAGGCCACGTGTCTTGTCCAGAGCTC GATATCGATACACGTCTGCAGTCAACTGGAATTTTCAT GATTGAATTTTGTAAGGTATTTTGAAATAATTTTTCAT ATAAAGGTGAGTTTGTATTAAAAGGTACTGGTGGAGTA TTTGATAGTGTATTAACCTTATGTGTGACATGTTCTAA TATAGTCACATTTTCATTATTTTTATTATAAGGCCTGC TGAAAATGACTGAATATAAACTTGTGGTAGTTGGAGCT GATGGCGTAGGCAAGAGTGCCTTGACGATACAGCTAAT TCAGAATCATTTTGTGGACGAATATGATCCAACAATAG AGGTAAATCTTGTTTTAATATGCATATTACTGGTGCAG |

TABLE 4-continued

Sequences for the amplified PCR fragments (726-730 bp) including the WT KRAS or mutated KRAS exon 2 fragments.

| Synthetic plasmid | Sequence (5'---3') |
|---|---|
| | GACCATTCTTTGATACAGATAAAGGTTTCTCTGACCAT TTTCATGAGTACTTATTACAAGATAATTATGCTGAAAG TTAAGTTATCTGAAATGTACCTTGGGTTTCAAGTTATA TGTAACCATTAATATGGGAACTTTACTTTCCTTGGGAG ATATCGGTACCTGGAGCACAAGACTGGCCTCATGGGCC TTCCGCTCACTGCCCGCTTTCCAGTCGGGAAACCTGTC GTGCCAGCTGCATTAACATGGTCATAGCTGTTTCCTTG CGTATTGG (SEQ ID NO: 23) |
| KRAS_G13D | GGTTTTCCCAGTCACGACGTTGTAAAACGACGGCCAGT GAGCGCGACGTAATACGACTCACTATAGGGCGAATTGG CGGAAGGCCGTCAAGGCCTAGGCGCGCCATGAGCTCGA TATCGATACACGTCTGCAGTCAACTGGAATTTTCATGA TTGAATTTTGTAAGGTATTTTGAAATAATTTTTCATAT AAAGGTGAGTTTGTATTAAAAGGTACTGGTGGAGTATT TGATAGTGTATTAACCTTATGTGTGACATGTTCTAATA TAGTCACATTTTCATTATTTTTATTATAAGGCCTGCTG AAAATGACTGAATATAAACTTGTGGTAGTTGGAGCTGG TGACGTAGGCAAGAGTGCCTTGACGATACAGCTAATTC AGAATCATTTTGTGGACGAATATGATCCAACAATAGAG GTAAATCTTGTTTTAATATGCATATTACTGGTGCAGGA CCATTCTTTGATACAGATAAAGGTTTCTCTGACCATTT TCATGAGTACTTATTACAAGATAATTATGCTGAAAGTT AAGTTATCTGAAATGTACCTTGGGTTTCAAGTTATATG TAACCATTAATATGGGAACTTTACTTTCCTTGGGAGAT ATCGGTACCTCTTAATTAACTGGCCTCATGGGCCTTCC GCTCACTGCCCGCTTTCCAGTCGGGAAACCTGTCGTGC CAGCTGCATTAACATGGTCATAGCTGTTTCCTTGCGTA TTGG (SEQ ID NO: 24) |
| KRAS_G12D & G13D | GGTTTTCCCAGTCACGACGTTGTAAAACGACGGCCAGT GAGCGCGACGTAATACGACTCACTATAGGGCGAATTGG CGGAAGGCCGTCAAGGCCACGTGTCTTGTCCAGAGCTC GATATCGATACACGTCTGCAGTCAACTGGAATTTTCAT GATTGAATTTTGTAAGGTATTTTGAAATAATTTTTCAT ATAAAGGTGAGTTTGTATTAAAAGGTACTGGTGGAGTA TTTGATAGTGTATTAACCTTATGTGTGACATGTTCTAA TATAGTCACATTTTCATTATTTTTATTATAAGGCCTGC TGAAAATGACTGAATATAAACTTGTGGTAGTTGGAGCT GATGACGTAGGCAAGAGTGCCTTGACGATACAGCTAAT TCAGAATCATTTTGTGGACGAATATGATCCAACAATAG AGGTAAATCTTGTTTTAATATGCATATTACTGGTGCAG GACCATTCTTTGATACAGATAAAGGTTTCTCTGACCAT TTTCATGAGTACTTATTACAAGATAATTATGCTGAAAG TTAAGTTATCTGAAATGTACCTTGGGTTTCAAGTTATA TGTAACCATTAATATGGGAACTTTACTTTCCTTGGGAG ATATCGGTACCTGGAGCACAAGACTGGCCTCATGGGCC TTCCGCTCACTGCCCGCTTTCCAGTCGGGAAACCTGTC GTGCCAGCTGCATTAACATGGTCATAGCTGTTTCCTTG CGTATTGG (SEQ ID NO: 25) |

TABLE 5

Oligos used for specific LDR for WT KRAS and mutated KRAS

| Synthetic plasmid | Oligo Name | Sequence (5'---3') |
|---|---|---|
| KRAS_WT | P1_WT | GCAAGCAGTGTCTTGCGCAAGCA GTGTCTTGCTAAGCGTACGTGCT TACACTCTTGCCTACGCCAC (SEQ ID NO: 28) |
| | P2_WT | Phosphate-CAGCTCCAACTAC CACAAG (SEQ ID NO: 29)- Biotin |
| KRAS_G12D | P1_G12D | GCAAGCAGTGTCTTGCGCAAGCA GTGTCTTGCTAAGCGTACGTGCT TACACTCTTGCCTACGCCAT (SEQ ID NO: 30) |
| | P2_G12D | Phosphate-CAGCTCCAACTAC CACAAG (SEQ ID NO: 31)- Biotin |
| KRAS_G13D | P1_G13D | CCTGACATGAATCAGGCCTGACA TGAATCAGGTAAGCGTACGTGCT TAAGGCACTCTTGCCTACGT (SEQ ID NO: 32) |
| | P2_G13D | Phosphate-CACCAGCTCCAAC TACCAC (SEQ ID NO: 33)- Biotin |

Example 7: DNP Selection

Figure 4:
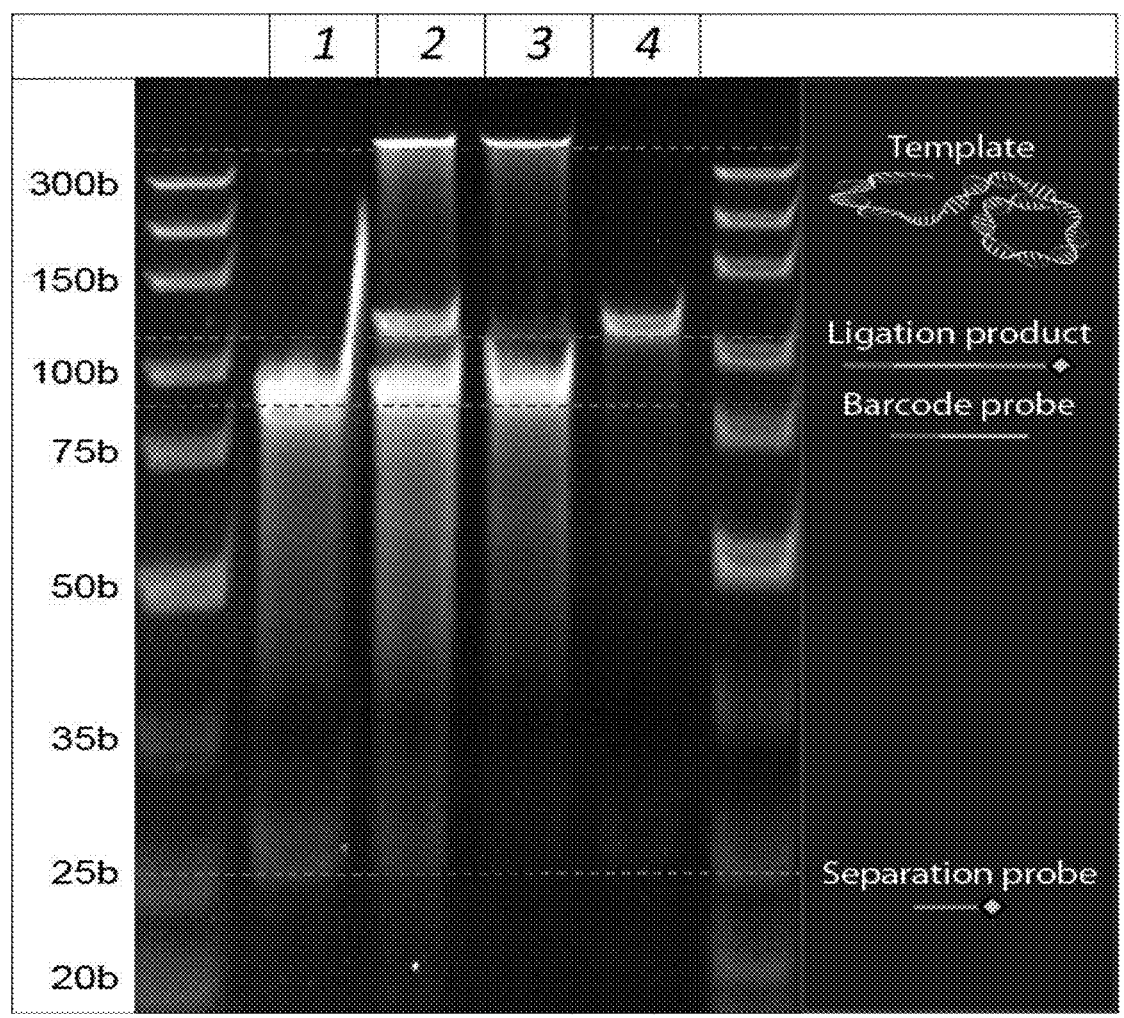
FIG. 4: A photograph of an SDS-PAGE gel showing purification of the DNPs using streptavidin beads. Lane 1 is a ligation control (no template), lane 2 is the ligation mix pre-separation, lane 3 is any nucleic acids that did not bind to the streptavidin coated beads and lane 4 is the final purified DNP product.

Following ligation, in order to separate the ligated products from the remainder of the molecules and to concentrate the sample for measurement, streptavidin-coated magnetic beads were used to capture only the fully formed DNPs. The remainder of the sample was washed away and then the DNP can be released from the bead (FIG. 4). The results for the purification of the DNP for the gyrA gene is shown in FIG. 4 in a 20% PAGE denaturing gel which tracks the process of the separation. The mix following ligation (FIG. 4, lane 2) contains bands of the bacterial template DNA, the DNP ligation product, the barcode probe and the separation probe. Following the immobilization of the ligation mix to the magnetic beads, a sample was taken from anything that did not bind to the beads (FIG. 4, lane 3). This shows that the template DNA and barcode probe did not bind to the beads, as expected. The vast majority of DNPs and separation probe bound to the beads (FIG. 4, lane 4). A very high degree of purity was achieved via the streptavidin coated magnetic bead separation.

Figure 5A:
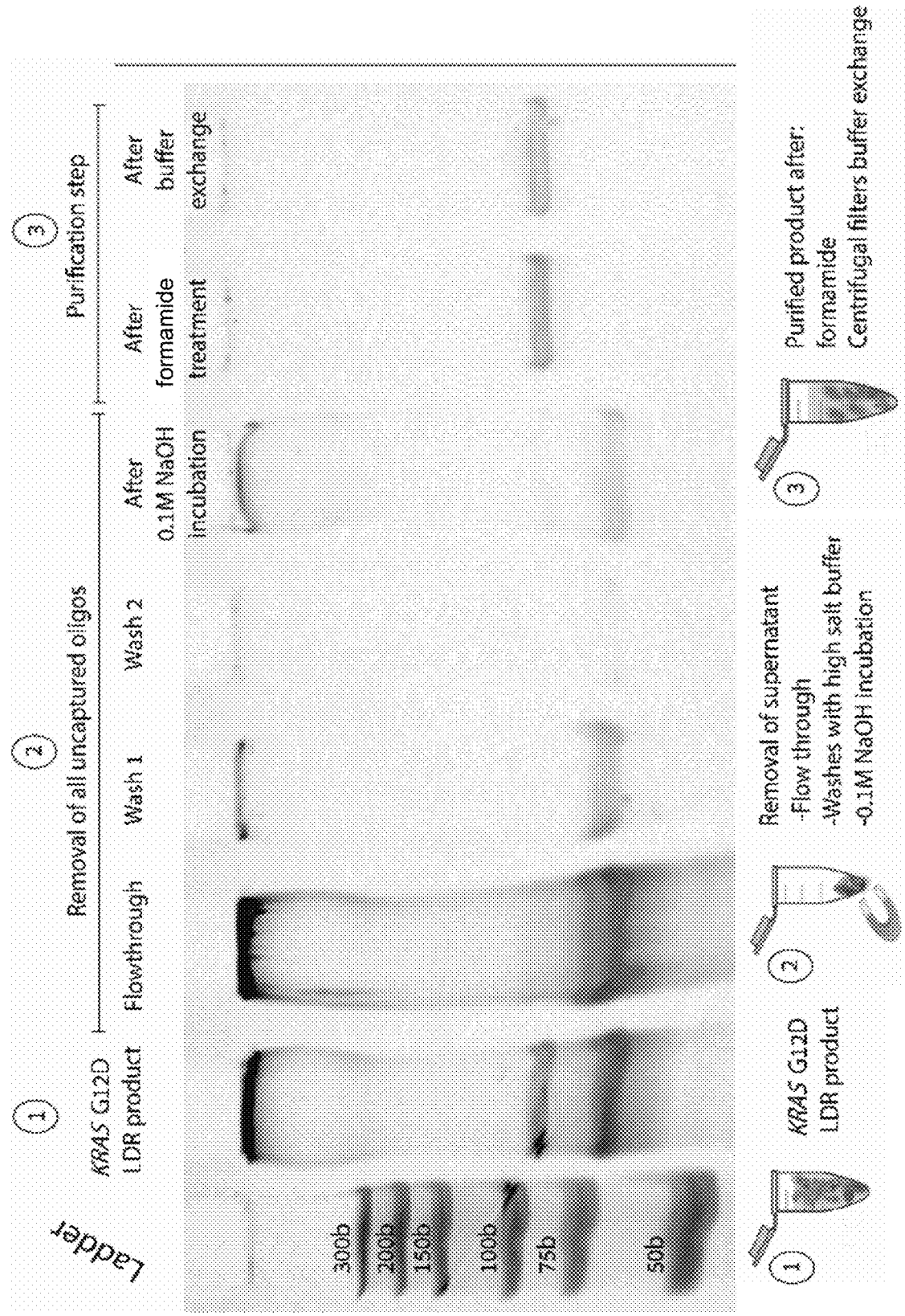
FIGS. 5A-B: Photographs of SDS-PAGE gels showing (5A) the full separation protocol including buffer exchange for the KRAS G12D purification and (5B) the final result of purification for WT KRAS and both KRAS mutants.
Figure 5B:

As shown in FIG. 5, a similar purification assay using magnetic beads was performed for the KRAS ligation product. The DNPs on the beads were washed using a high salt buffer, which was followed by formamide treatment which causes the DNP to dissociate from the beads. Finally, a buffer exchange was performed so that the DNPs were in a buffer suitable for nanopore analysis (FIG. 5A). The purification results for WT KRAS and both mutants are provided in FIG. 5B.

Example 8: Labeled Beacon Hybridization

Figure 6:
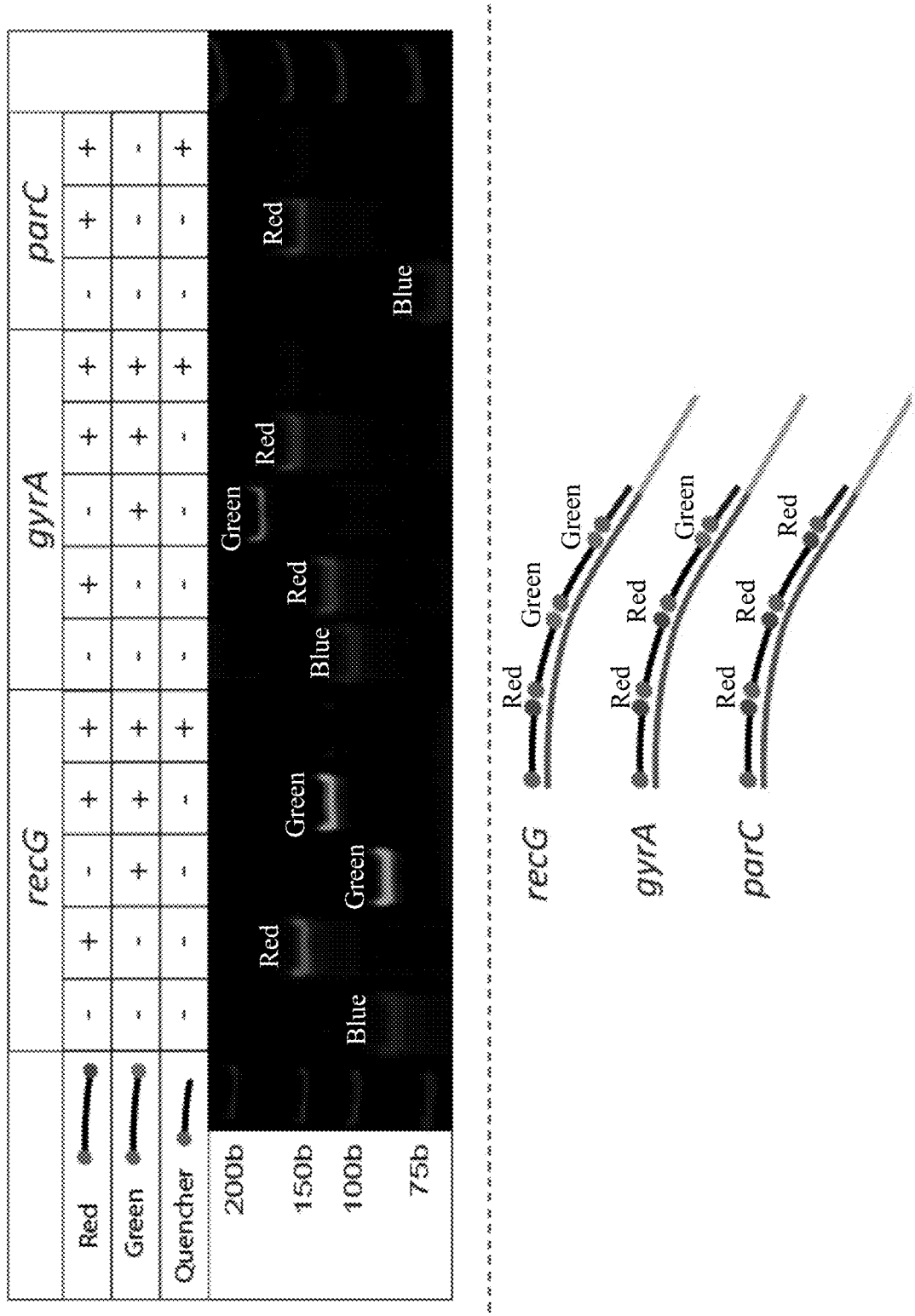
FIG. 6: Photograph of a native PAGE gel showing analysis of the hybridization reactions for each possible beacon combination to verify that hybridization is occurring properly. Red, Green and quencher-only beacons are added to each barcode probe individually and all simultaneously and then imaged using a 3-laser gel scanner. A schematic of the binding of the beacons to each template is shown below.

The purified DNPs, each containing a unique barcode probe, were hybridized to labeled beacons which each characterize their respective barcode. Each labeled beacon is an oligonucleotide which contains a fluorophore on the 5' end and a quencher on the 3' end (see Table 6). Each color label corresponds to a unique DNA sequence which allows it to hybridize to a specific region of the barcode probe. Hybridization was verified by adding each beacon combination to all three barcode probes (FIG. 6). Native PAGE, a gel performed at room temperature, allowed for confirmation that the correct color photons are being emitted, which indicates proper hybridization has occurred. The gel is performed at room temperature, as at high temperatures the beacons will disassociate from the DNP. However, this allows for DNPs to form secondary structures which can alter where their band is located on the gel. Therefore, the band locations are not indicative of the size and molecular weight of the sample. This can be observed in recG+red beacon and gyrA+green beacon. Both of these have very high bands, which indicates secondary structures formation.

TABLE 6

Beacons used for the hybridization step

| Beacon # | Labeling color | Sequence (5'---3') |
|---|---|---|
| 1 | — | GACCTAATGCATC (SEQ ID NO: 34)-Quencher |
| 2 | Red | Fluorophore-CGTTATGTGACGAACG (SEQ ID NO: 35)-Quencher |
| 3 | Green | Fluorophore-CGACCGTACCTAGTCG (SEQ ID NO: 36)-Quencher |
| 4 | Red | Fluorophore-CCTGGTCAGACTCAGG (SEQ ID NO: 37)-Quencher |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A method for single-molecule detection of a nucleic acid variant in a sample, comprising:
   a. providing a sample containing nucleic acids;
   b. contacting said sample with at least one first molecule comprising: a nanopore-sensible barcode linked to nucleic acids complementary to a first sequence, said first sequence comprising a first region of a nucleic acid template adjacent to said variant; and at least one second molecule comprising: a selection marker linked to nucleic acids complementary to a second sequence, said second sequence comprising a second region contiguous to said first sequence in said nucleic acid template, wherein:
   i. said first or second sequence further comprises said variant at an end of said first or second sequence;
   ii. said first molecule does not comprise said selection marker and comprises complementarity to only one region in said nucleic acid template;
   iii. said second molecule does not comprise said nanopore-sensible barcode and comprises complementarity to only one region in said nucleic acid template;
   iv. said barcode comprises a DNA sequence; and
   v. said nanopore sensible barcode is at the 5' end or 3' end of said at least one first molecule;
   c. contacting said sample with a ligase;
   d. isolating a composition containing said selection marker;
   e. hybridizing said barcode to a molecular beacon; and
   f. passing said composition through at least one nanopore configured to sense said molecular beacon;
   thereby detecting a single molecule of a nucleic acid variant in a sample.

2. The method of claim 1, wherein said nucleic acid variant is selected from the group consisting of: a single nucleotide variation, an insertion, a deletion and a combination thereof.

3. The method of claim 1, wherein said nucleic acid variant is at an end of said first sequence not linked to said barcode or an end of said second sequence not linked to said selection marker and said first and second sequences are contiguous at said variant.

4. The method of claim 1, wherein said barcode is linked to a 5' end of said nucleic acids and said selection marker is linked to a 3' end of said nucleic acids or said barcode is linked to a 3' end of said nucleic acids and said selection marker is linked to a 5' end of said nucleic acids.

5. The method of claim 1, wherein a 5' end of said nucleic acids complementary to a first sequence or a second sequence not linked to said barcode or said selection marker contains a 5' phosphorylation.

6. The method of claim 1, wherein said sample containing nucleic acids comprises said nucleic acid template comprising said variant, and wherein said barcode, said selection marker, and said nucleic acid template comprising said variant form a single molecule following contact with said ligase.

7. The method of claim 1, for unique detection of said nucleic acid variant, wherein said variant is within close proximity to at least one other nucleic acid variant.

8. A composition comprising a nucleic acid template, a first molecule comprising: a nanopore-sensible barcode linked to nucleic acids complementary to a first portion of said nucleic acid template, and a second molecule comprising: a selection marker linked to nucleic acids complementary to a second portion of said nucleic acid template, wherein:

a. said first portion and said second portion are contiguous on said nucleic acid template,
b. said first molecule does not comprise said selection marker and comprises complementarity to only one region in said nucleic acid template,
c. said second molecule does not comprise said nanopore-sensible barcode and comprises complementarity to only one region in said nucleic acid template,
d. said nanopore sensible barcode comprises a DNA sequence and said DNA sequence is hybridized to a molecular beacon,
e. said nanopore sensible barcode is at the 5' end or 3' end of said first molecule, and
f. said nucleic acids complementary to a first portion and said nucleic acids complementary to a second portion are ligated together.

9. The composition of claim 8, wherein said nucleic acid template comprises a nucleic acid variant.

10. The composition of claim 9, wherein said nucleic acid variant is at an end of said first portion of said nucleic acid template and is directly ligated to said second portion.

11. The composition of claim 8, wherein said selection marker is selected from the group consisting of: biotin, His peptide, human influenza hemagglutinin (HA) protein, glutathione-S-transferase (GST) protein, chitin binding protein (CBP) protein, maltose binding protein (MBP) protein, Myc polypeptide, NE peptide and FLAG polypeptide.

12. The composition of claim 8, for use in the detection or identification of a nucleic acid variant.

13. A kit comprising:
a. a first molecule comprising at least one nanopore-sensible barcode and complementarity to only one region in a target nucleic acid template molecule, wherein said nanopore sensible barcode comprises a DNA sequence or a bulky group and is at the 5' end or 3' end of said first molecule;
b. a second molecule comprising at least one selection marker and complementarity to only one region in a target nucleic acid template molecule;
c. at least one molecular beacon configured to hybridize to said nanopore-sensible barcode; and
d. at least one ligase,
   wherein said first molecule does not comprise said selection marker and said second molecule does not comprise said nanopore-sensible barcode.

14. The method of claim 1, wherein said contacting with a ligase produces a ligation product, said isolating a composition comprises isolating said ligation product, said passing through at least one nanopore comprises passing said ligation product through at least one nanopore and said method does not comprise amplifying said ligation product.

15. The method of claim 1, wherein said method is a multiplex method of detecting a plurality of nucleic acid variants in a sample, wherein said method comprises contacting said sample with at least two first molecules and at least two second molecules, wherein a first first molecule and a first second molecule comprise sequences that are contiguous at a first variant, said second first molecule and said second second molecule comprises sequences that are contiguous at a second variant, wherein all second molecules comprises the same selection marker and wherein each nanopore sensible barcode uniquely identifies the variant to which it is adjacent such that said passing comprises identifying the presence of one or more variants based on the sensing of said one or more variants unique barcode.

16. The method of claim 1, wherein said sample is a bodily fluid and wherein said method is method of detecting a nucleic acid variant in circulating tumor DNA (ctDNA).

* * * * *

SEQUENCE LISTING

```
<160> NUMBER OF SEQ ID NOS: 37

<210> SEQ ID NO 1
<211> LENGTH: 940
<212> TYPE: DNA
<213> ORGANISM: Staphylococcus aureus

<400> SEQUENCE: 1
ttgaaggagg aactcttgat ggctgaatta cctcaatcaa gaataaatga acgaaatatt      60
accagtgaaa tgcgtgaatc attttttagat tatgcgatga gtgttatcgt tgctcgtgca    120
ttgccagatg ttcgtgacgg tttaaaacca gtacatcgtc gtatactata tggattaaat    180
gaacaaggta tgacaccgga taaatcatat aaaaaatcag cacgtatcgt tggtgacgta    240
atgggtaaat atcaccctca tggtgactca tctatttatg aagcaatggt acgtatggct    300
caagatttca gttatcgtta tccgcttgtt gatggccaag gtaactttgg ttcaatggat    360
ggagatggcg cagcagcaat gcgttatact gaagcgcgta tgactaaaat cacacttgaa    420
ctgttacgtg atattaataa agatacaata gatttttatcg ataactatga tggtaatgaa    480
agagagccgt cagtcttacc tgctcgattc cctaacttat tagccaatgg tgcatcaggt    540
atcgcggtag gtatggcaac gaatattcca ccacataact aacagaatt aatcaatggt    600 gtacttagct taagtaagaa ccctgatatt tcaattgctg agttaatgga ggatattgaa    660
ggtcctgatt tcccaactgc tggacttatt ttaggtaaga gtggtattag acgtgcatat    720
gaaacaggtc gtggttcaat tcaaatgcgt tctcgtgcag ttattgaaga acgtggaggc    780
ggacgtcaac gtattgttgt cactgaaatt cctttccaag tgaataaggc tcgtatgatt    840
gaaaaaattg cagagctcgt tcgtgacaag aaaattgacg gtatcactga tttacgtgat    900
gaaacaagtt tacgtactgg tgtgcgtgtc gttattgatg                          940

<210> SEQ ID NO 2
<211> LENGTH: 940
<212> TYPE: DNA
<213> ORGANISM: Staphylococcus aureus

<400> SEQUENCE: 2
ttgaaggagg aactcttgat ggctgaatta cctcaatcaa gaataaatga acgaaatatt      60
accagtgaaa tgcgtgaatc attttttagat tatgcgatga gtgttatcgt tgctcgtgca    120
```

-continued

| | |
|---|---|
| ttgccagatg ttcgtgacgg tttaaaacca gtacatcgtc gtatactata tggattaaat | 180 |
| gaacaaggta tgacaccgga taaatcatat aaaaaatcag cacgtatcgt tggtgacgta | 240 |
| atgggtaaat atcaccctca tggtgactta tctatttatg aagcaatggt acgtatggct | 300 |
| caagatttca gttatcgtta tccgcttgtt gatggccaag gtaactttgg ttcaatggat | 360 |
| ggagatggcg cagcagcaat gcgttatact gaagcgcgta tgactaaaat cacacttgaa | 420 |
| ctgttacgtg atattaataa agatacaata gattttatcg ataactatga tggtaatgaa | 480 |
| agagagccgt cagtcttacc tgctcgattc cctaacttat tagccaatgg tgcatcaggt | 540 |
| atcgcggtag gtatggcaac gaatattcca ccacataact aacagaatt aatcaatggt | 600 |
| gtacttagct aagtaagaa ccctgatatt tcaattgctg agttaatgga ggatattgaa | 660 |
| ggtcctgatt tcccaactgc tggacttatt ttaggtaaga gtggattag acgtgcatat | 720 |
| gaaacaggtc gtggttcaat tcaaatgcgt tctcgtgcag ttattgaaga acgtggaggc | 780 |
| ggacgtcaac gtattgttgt cactgaaatt cctttccaag tgaataaggc tcgtatgatt | 840 |
| gaaaaaattg cagagctcgt tcgtgacaag aaaattgacg gtatcactga tttacgtgat | 900 |
| gaaacaagtt tacgtactgg tgtgcgtgtc gttattgatg | 940 |

<210> SEQ ID NO 3
<211> LENGTH: 943
<212> TYPE: DNA
<213> ORGANISM: Staphylococcus aureus

<400> SEQUENCE: 3

| | |
|---|---|
| ttgaaggagg aactcttgat ggctgaatta cctcaatcaa gaataaatga acgaaatatt | 60 |
| accagtgaaa tgcgtgaatc atttttagat tatgcgatga gtgttatcgt tgctcgtgca | 120 |
| ttgccagatg ttcgtgacgg tttaaaacca gtacatcgtc gtatactata tggattaaat | 180 |
| gaacaaggta tgacaccgga taaatcatat aaaaaatcag cacgtatcgt tggtgacgta | 240 |
| atgggtaaat atcaccctca tggtgactca tctatttatg aagcaatggt acgtatggct | 300 |
| caagatttca gttatcgtta tccgcttgtt gatggccaag gtaactttgg ttcaatggat | 360 |
| ggagatggcg cagcagcaat gcgttatact gaagcgcgta tgactaaaat cacacttgaa | 420 |
| ctgttacgtg atattaataa agatacaata gattttatcg ataactatga tggtaatgaa | 480 |
| agagagccgt cagtcttacc tgctcgattc cctaacttat tagccaatgg tgcatcaggt | 540 |
| atcgcggtag gtatggcaac gaatattcca ccacataact aacagaatt aatcaatggt | 600 |
| gtacttagct aagtaagaa ccctgatatt tcaattgctg agttaatgga ggatattgaa | 660 |
| ggtcctgatt tcccaactgc tggacttatt ttaggtaaga gtggtattat tagacgtgca | 720 |
| tatgaaacag gtcgtggttc aattcaaatg cgttctcgtg cagttattga agaacgtgga | 780 |
| ggcggacgtc aacgtattgt tgtcactgaa attccttttcc aagtgaataa ggctcgtatg | 840 |
| attgaaaaaa ttgcagagct cgttcgtgac aagaaaattg acggtatcac tgatttacgt | 900 |
| gatgaaacaa gtttacgtac tggtgtgcgt gtcgttattg atg | 943 |

<210> SEQ ID NO 4
<211> LENGTH: 885
<212> TYPE: DNA
<213> ORGANISM: Staphylococcus aureus

<400> SEQUENCE: 4

| | |
|---|---|
| gatgaggagg aaatctagtg agtgaaataa ttcaagattt atcacttgaa gatgttttag | 60 |

-continued

```
gtgatcgctt tggaagatat agtaaatata ttattcaaga gcgtgcattg ccagatgttc      120
gtgatggttt aaaaccagta caacgtcgta ttttatatgc aatgtattca agtggtaata      180
cacacgataa aaatttccgt aaaagtgcga aaacagtcgg tgatgttatt ggtcaatatc      240
atccacatgg agactcctca gtgtacgaag caatggtccg tttaagtcaa gactggaagt      300
tacgacatgt cttaatagaa atgcatggta ataatggtag tatcgataat gatccgccag      360
cggcaatgcg ttacactgaa gctaagttaa gcttactagc tgaagagtta ttacgtgata      420
ttaataaaga gacagtttct ttcattccaa actatgatga tacgacactc gaaccaatgg      480
tattgccatc aagatttcct aacttactag tgaatggttc tacaggtata tctgcaggtt      540
acgcgacaga tataccacca cataatttag ctgaagtgat tcaagcaaca cttaaatata      600
ttgataatcc ggatattaca gtcaatcaat taatgaaata tattaaaggt cctgattttc      660
caactggtgg tattattcaa ggtattgatg gtattaaaaa agcttatgaa tcaggtaaag      720
gtagaattat agttcgttct aaagttgaag aagaaacttt acgcaatgga cgtaaacagt      780
taattattac tgaaattcca tatgaagtga acaaaagtag cttagtaaaa cgtatcgatg      840
aattacgtgc tgacaaaaaa gtcgatggta tcgttgaagt acgtg                     885
```

<210> SEQ ID NO 5
<211> LENGTH: 885
<212> TYPE: DNA
<213> ORGANISM: Staphylococcus aureus

<400> SEQUENCE: 5

```
gatgaggagg aaatctagtg agtgaaataa ttcaagattt atcacttgaa gatgttttag       60
gtgatcgctt tggaagatat agtaaatata ttattcaaga gcgtgcattg ccagatgttc      120
gtgatggttt aaaaccagta caacgtcgta ttttatatgc aatgtattca agtggtaata      180
cacacgataa aaatttccgt aaaagtgcga aaacagtcgg tgatgttatt ggtcaatatc      240
atccacatgg agactactca gtgtacgaag caatggtccg tttaagtcaa gactggaagt      300
tacgacatgt cttaatagaa atgcatggta ataatggtag tatcgataat gatccgccag      360
cggcaatgcg ttacactgaa gctaagttaa gcttactagc tgaagagtta ttacgtgata      420
ttaataaaga gacagtttct ttcattccaa actatgatga tacgacactc gaaccaatgg      480
tattgccatc aagatttcct aacttactag tgaatggttc tacaggtata tctgcaggtt      540
acgcgacaga tataccacca cataatttag ctgaagtgat tcaagcaaca cttaaatata      600
ttgataatcc ggatattaca gtcaatcaat taatgaaata tattaaaggt cctgattttc      660
caactggtgg tattattcaa ggtattgatg gtattaaaaa agcttatgaa tcaggtaaag      720
gtagaattat agttcgttct aaagttgaag aagaaacttt acgcaatgga cgtaaacagt      780
taattattac tgaaattcca tatgaagtga acaaaagtag cttagtaaaa cgtatcgatg      840
aattacgtgc tgacaaaaaa gtcgatggta tcgttgaagt acgtg                     885
```

<210> SEQ ID NO 6
<211> LENGTH: 885
<212> TYPE: DNA
<213> ORGANISM: Staphylococcus aureus

<400> SEQUENCE: 6

```
gatgaggagg aaatctagtg agtgaaataa ttcaagattt atcacttgaa gatgttttag       60
gtgatcgctt tggaagatat agtaaatata ttattcaaga gcgtgcattg ccagatgttc      120
gtgatggttt aaaaccagta caacgtcgta ttttatatgc aatgtattca agtggtaata      180
```

```
cacacgataa aaatttccgt aaaagtgcga aaacagtcgg tgatgttatt ggtcaatatc    240
atccacatgg agactcctca gtgtacgaag caatggtccg tttaagtcaa gactggaagt    300
tacgacatgt cttaatagaa atgcatggta ataatggtag tatcgataat gatccgccag    360
cggcaatgcg ttacactgaa gctaagttaa gcttactagc tgaagagtta ttacgtgata    420
ttaataaaga gacagtttct ttcattccaa actatgatga tacgacactc gaaccaatgg    480
tattgccatc aagatttcct aacttactag tgaatggttc tacaggtata tctgcaggtt    540
acgcgacaga tataccacca cataatttag ctgaagtgat tcaagcaaca cttaaatata    600
ttgataatcc ggatattaca gtcaatcaat aatgaaata tattaaaggt cctgattttc    660
caactggtgg tattattcaa ggtattgatg gtattaaaaa agcttatgaa tcaggtaaag    720
gtagaattat agttcgttct aaagttgaag aagaaacttt acgcaatgga cgtaaacagt    780
taattattac tgaaattcca tatgaagtga acaaaagtag cttagtaaaa cgtatcgatg    840
aattacgtgc tgacaaaaaa gtcgatggta tcgttgaagt acgtg              885
```

```
<210> SEQ ID NO 7
<211> LENGTH: 520
<212> TYPE: DNA
<213> ORGANISM: Staphylococcus aureus

<400> SEQUENCE: 7
caacagtatt atggtgtttc ccgtgtaggg ttattgcatg gtaagttatc tgccgatgaa     60
aaagatgagg tcatgcaaaa gtttagtaat catgagataa atgttttagt ttctactact    120
gttgttgaag taggtgttaa tgtaccgaat gcaacttttta tgatgattta tgatgcggat   180
cgctttggat tatcaacttt acatcagtta cgcggtcgtg taggtagaag tgaccagcaa    240
agttactgtg tttttaattgc atcccctaaa acagaaacag gaattgaaag aatgacaatt    300
atgacacaaa caacggatgg atttgaattg agtgaacgag acttagaaat gcgtggtcct    360
ggagatttct ttggtgttaa acaaagtgga ttgccagatt tcttagttgc caatttagtt    420
gaaggttatc gtatgttaga agttgctcgt gatgaagcag ctgaacttat tcaatctggc    480
gtattctttg aaaatacgta tcaacattta cgtcattttg                          520
```

```
<210> SEQ ID NO 8
<211> LENGTH: 520
<212> TYPE: DNA
<213> ORGANISM: Staphylococcus aureus

<400> SEQUENCE: 8
caacagtatt atggtgtttc ccgtgtaggg ttattgcatg gtaagttatc tgccgatgaa     60
aaagatgagg tcatgcaaaa gtttagtaat catgagataa atgttttagt ttctactact    120
gttgttgaag taggtgttaa tgtaccgaat gcaacttttta tgatgattta tgatgcggat   180
cgctttggat tatcaacttt acatcagtta cgcggtcgtg taggtagaag tgaccagcaa    240
agttactgtg tttttaattgc atcccctaaa acagaaacag gaattgaaag aatgacaatt    300
atgacacaaa caacggatgg atttgaattg agtgaacgag acttagaaat gcgtggtcct    360
ggagatttct ttggtgttaa acaaagtgga ttgccagatt tcttagttgc caatttagtt    420
gaagattatc gtatgttaga agttgctcgt gatgaagcag ctgaacttat tcaatctggc    480
gtattctttg aaaatacgta tcaacattta cgtcattttg                          520
```

```
<210> SEQ ID NO 9
```

```
<211> LENGTH: 520
<212> TYPE: DNA
<213> ORGANISM: Staphylococcus aureus

<400> SEQUENCE: 9
caacagtatt atggtgtttc ccgtgtaggg ttattgcatg gtaagttatc tgccgatgaa      60
aaagatgagg tcatgcaaaa gtttagtaat catgagataa atgttttagt ttctactact     120
gttgttgaag taggtgttaa tgtaccgaat gcaacttttta tgatgattta tgatgcggat    180
cgctttggat tatcaacttt acatcagtta cgcggtcgtg taggtagaag tgaccagcaa     240
agttactgtg tttttaattgc atcccctaaa acagaaacag gaattgaaag aatgacaatt    300
atgacacaaa caacggatgg atttgaattg agtgaacgag acttagaaat gcgtggtcct    360
ggagatttct ttggtgttaa acaaagtgga ttgccagatt tcttagttgc caatttagtt    420
gaagattatc gtatgttaga agttgctcgt gatgaagcag ctgaacttat tcaatctggc   480
gtattctttg aaaatacgta tcaacattta cgtcattttg                          520

<210> SEQ ID NO 10
<211> LENGTH: 22
<212> TYPE: DNA
<213> ORGANISM: Staphylococcus aureus

<400> SEQUENCE: 10
ttgaaggagg aactcttgat gg                                              22

<210> SEQ ID NO 11
<211> LENGTH: 20
<212> TYPE: DNA
<213> ORGANISM: Staphylococcus aureus

<400> SEQUENCE: 11
catcaataac gacacgcaca                                                 20

<210> SEQ ID NO 12
<211> LENGTH: 20
<212> TYPE: DNA
<213> ORGANISM: Staphylococcus aureus

<400> SEQUENCE: 12
gatgaggagg aaatctagtg                                                 20

<210> SEQ ID NO 13
<211> LENGTH: 23
<212> TYPE: DNA
<213> ORGANISM: Staphylococcus aureus

<400> SEQUENCE: 13
cacgtacttc aacgatacca tcg                                             23

<210> SEQ ID NO 14
<211> LENGTH: 22
<212> TYPE: DNA
<213> ORGANISM: Staphylococcus aureus

<400> SEQUENCE: 14
caacagtatt atggtgtttc cc                                              22

<210> SEQ ID NO 15
<211> LENGTH: 24
<212> TYPE: DNA
<213> ORGANISM: Staphylococcus aureus
```

```
<400> SEQUENCE: 15
caaaatgacg taaatgttga tacg                                         24

<210> SEQ ID NO 16
<211> LENGTH: 89
<212> TYPE: DNA
<213> ORGANISM: Artificial
<220> FEATURE:
<223> OTHER INFORMATION: Synthetic

<400> SEQUENCE: 16
cgttcgtcac ataacgcctc acatcacgga gggttcgtca cataacggat gcattaggtc   60
gctggactta ttttaggtaa gagtggtat                                    89

<210> SEQ ID NO 17
<211> LENGTH: 26
<212> TYPE: DNA
<213> ORGANISM: Staphylococcus aureus

<400> SEQUENCE: 17
tattagacgt gcatatgaaa caggtc                                       26

<210> SEQ ID NO 18
<211> LENGTH: 86
<212> TYPE: DNA
<213> ORGANISM: Artificial
<220> FEATURE:
<223> OTHER INFORMATION: Synthetic

<400> SEQUENCE: 18
cgactaggta cggtcgcgac taggtacggt cgcgactagg tacggtcgga tgcattaggt   60
cgtcaatatc atccacatgg agactc                                       86

<210> SEQ ID NO 19
<211> LENGTH: 22
<212> TYPE: DNA
<213> ORGANISM: Staphylococcus aureus

<400> SEQUENCE: 19
ctcagtgtac gaagcaatgg tc                                           22

<210> SEQ ID NO 20
<211> LENGTH: 85
<212> TYPE: DNA
<213> ORGANISM: Artificial
<220> FEATURE:
<223> OTHER INFORMATION: Synthetic

<400> SEQUENCE: 20
cgactaggta cggtcgcgtt cgtcacataa cgcgttcgtc acataacgga tgcattaggt   60
ccttagttgc caatttagtt gaagg                                        85

<210> SEQ ID NO 21
<211> LENGTH: 24
<212> TYPE: DNA
<213> ORGANISM: Staphylococcus aureus

<400> SEQUENCE: 21
ttatcgtatg ttagaagttg ctcg                                         24

<210> SEQ ID NO 22
```

<211> LENGTH: 726
<212> TYPE: DNA
<213> ORGANISM: Homo sapiens

<400> SEQUENCE: 22

```
ggttttccca gtcacgacgt tgtaaaacga cggccagtga gcgcgacgta atacgactca      60
ctatagggcg aattggcgga aggccgtcaa ggcctaggcg cgccatgagc tcgatatcga     120
tacacgtctg cagtcaactg gaattttcat gattgaattt tgtaaggtat tttgaaataa     180
ttttttcatat aaaggtgagt ttgtattaaa aggtactggt ggagtatttg atagtgtatt    240
aaccttatgt gtgacatgtt ctaatatagt cacattttca ttatttttat tataaggcct     300
gctgaaaatg actgaatata aacttgtggt agttggagct ggtggcgtag caagagtgc      360
cttgacgata cagctaattc agaatcattt tgtggacgaa tatgatccaa caatagaggt     420
aaatcttgtt ttaatatgca tattactggt gcaggaccat tctttgatac agataaaggt     480
ttctctgacc attttcatga gtacttatta caagataatt atgctgaaag ttaagttatc     540
tgaaatgtac cttgggtttc aagttatatg taaccattaa tatgggaact ttactttcct    600
tgggagatat cggtacctct taattaactg gcctcatggg ccttccgctc actgcccgct     660
ttccagtcgg gaaacctgtc gtgccagctg cattaacatg gtcatagctg tttccttgcg     720
tattgg                                                                726
```

<210> SEQ ID NO 23
<211> LENGTH: 730
<212> TYPE: DNA
<213> ORGANISM: Homo sapiens

<400> SEQUENCE: 23

```
ggttttccca gtcacgacgt tgtaaaacga cggccagtga gcgcgacgta atacgactca      60
ctatagggcg aattggcgga aggccgtcaa ggccacgtgt cttgtccaga gctcgatatc     120
gatacacgtc tgcagtcaac tggaattttc atgattgaat tttgtaaggt attttgaaat     180
aattttttcat ataaaggtga gtttgtatta aaggtactgg tggagtatt tgatagtgta    240
ttaaccttat gtgtgacatg ttctaatata gtcacatttt cattattttt attataaggc     300
ctgctgaaaa tgactgaata taaacttgtg gtagttggag ctgatggcgt aggcaagagt     360
gccttgacga tacagctaat tcagaatcat tttgtggacg aatatgatcc aacaatagag     420
gtaaatcttg ttttaatatg catattactg gtgcaggacc attctttgat acagataaag     480
gtttctctga ccattttcat gagtacttat acaagataa ttatgctgaa agttaagtta     540
tctgaaatgt accttgggtt tcaagttata tgtaaccatt aatatgggaa ctttactttc     600
cttgggagat atcggtacct ggagcacaag actggcctca tgggccttcc gctcactgcc     660
cgcttttccag tcgggaaacc tgtcgtgcca gctgcattaa catggtcata gctgtttcct     720
tgcgtattgg                                                            730
```

<210> SEQ ID NO 24
<211> LENGTH: 726
<212> TYPE: DNA
<213> ORGANISM: Homo sapiens

<400> SEQUENCE: 24

```
ggttttccca gtcacgacgt tgtaaaacga cggccagtga gcgcgacgta atacgactca      60
ctatagggcg aattggcgga aggccgtcaa ggcctaggcg cgccatgagc tcgatatcga     120
tacacgtctg cagtcaactg gaattttcat gattgaattt tgtaaggtat tttgaaataa     180
```

```
ttttcatat aaaggtgagt ttgtattaaa aggtactggt ggagtatttg atagtgtatt      240
aaccttatgt gtgacatgtt ctaatatagt cacattttca ttattttat tataaggcct      300 gctgaaaatg actgaatata aacttgtggt agttggagct ggtgacgtag caagagtgc      360 cttgacgata cagctaattc agaatcattt tgtggacgaa tatgatccaa caatagaggt      420
aaatcttgtt ttaatatgca tattactggt gcaggaccat tctttgatac agataaaggt      480
ttctctgacc atttcatga gtacttatta caagataatt atgctgaaag ttaagttatc      540
tgaaatgtac cttgggtttc aagttatatg taaccattaa tatgggaact ttactttcct      600
tgggagatat cggtacctct taattaactg gcctcatggg ccttccgctc actgcccgct      660
ttccagtcgg gaaacctgtc gtgccagctg cattaacatg gtcatagctg tttccttgcg      720
tattgg                                                                 726
```

```
<210> SEQ ID NO 25
<211> LENGTH: 730
<212> TYPE: DNA
<213> ORGANISM: Homo sapiens

<400> SEQUENCE: 25
ggttttccca gtcacgacgt tgtaaaacga cggccagtga gcgcgacgta atacgactca       60
ctatagggcg aattggcgga aggccgtcaa ggccacgtgt cttgtccaga gctcgatatc      120
gatacacgtc tgcagtcaac tggaattttc atgattgaat tttgtaaggt attttgaaat      180 aattttcat ataaaggtga gtttgtatta aaggtactg gtggagtatt tgatagtgta       240
ttaaccttat gtgtgacatg ttctaatata gtcacatttt cattattttt attataaggc      300
ctgctgaaaa tgactgaata taaacttgtg gtagttggag ctgatgacgt aggcaagagt      360
gccttgacga tacagctaat tcagaatcat tttgtggacg aatatgatcc aacaatagag      420
gtaaatcttg ttttaatatg catattactg gtgcaggacc attctttgat acagataaag      480
gtttctctga ccattttcat gagtacttat acaagataa ttatgctgaa agttaagtta      540
tctgaaatgt accttgggtt tcaagttata tgtaaccatt aatatgggaa ctttactttc      600
cttgggagat atcggtacct ggagcacaag actggcctca tgggccttcc gctcactgcc      660
cgctttccag tcgggaaacc tgtcgtgcca gctgcattaa catggtcata gctgtttcct      720
tgcgtattgg                                                             730
```

```
<210> SEQ ID NO 26
<211> LENGTH: 19
<212> TYPE: DNA
<213> ORGANISM: Homo sapiens

<400> SEQUENCE: 26
ggttttccca gtcacgacg                                                    19
```

```
<210> SEQ ID NO 27
<211> LENGTH: 20
<212> TYPE: DNA
<213> ORGANISM: Homo sapiens

<400> SEQUENCE: 27
ccaatacgca aggaaacagc                                                   20
```

```
<210> SEQ ID NO 28
<211> LENGTH: 66
<212> TYPE: DNA
```

```
<213> ORGANISM: Artificial
<220> FEATURE:
<223> OTHER INFORMATION: Synthetic

<400> SEQUENCE: 28
gcaagcagtg tcttgcgcaa gcagtgtctt gctaagcgta cgtgcttaca ctcttgccta    60
cgccac                                                               66

<210> SEQ ID NO 29
<211> LENGTH: 19
<212> TYPE: DNA
<213> ORGANISM: Homo sapiens

<400> SEQUENCE: 29
cagctccaac taccacaag                                                 19

<210> SEQ ID NO 30
<211> LENGTH: 66
<212> TYPE: DNA
<213> ORGANISM: Artificial
<220> FEATURE:
<223> OTHER INFORMATION: Synthetic

<400> SEQUENCE: 30
gcaagcagtg tcttgcgcaa gcagtgtctt gctaagcgta cgtgcttaca ctcttgccta    60
cgccat                                                               66

<210> SEQ ID NO 31
<211> LENGTH: 19
<212> TYPE: DNA
<213> ORGANISM: Homo sapiens

<400> SEQUENCE: 31
cagctccaac taccacaag                                                 19

<210> SEQ ID NO 32
<211> LENGTH: 66
<212> TYPE: DNA
<213> ORGANISM: Artificial
<220> FEATURE:
<223> OTHER INFORMATION: Synthetic

<400> SEQUENCE: 32
cctgacatga atcaggcctg acatgaatca ggtaagcgta cgtgcttaag gcactcttgc    60
ctacgt                                                               66

<210> SEQ ID NO 33
<211> LENGTH: 19
<212> TYPE: DNA
<213> ORGANISM: Homo sapiens

<400> SEQUENCE: 33
caccagctcc aactaccac                                                 19

<210> SEQ ID NO 34
<211> LENGTH: 13
<212> TYPE: DNA
<213> ORGANISM: Artificial
<220> FEATURE:
<223> OTHER INFORMATION: Synthetic

<400> SEQUENCE: 34
gacctaatgc atc                                                       13
```

```
<210> SEQ ID NO 35
<211> LENGTH: 16
<212> TYPE: DNA
<213> ORGANISM: Artificial
<220> FEATURE:
<223> OTHER INFORMATION: Synthetic

<400> SEQUENCE: 35
cgttatgtga cgaacg                                                     16

<210> SEQ ID NO 36
<211> LENGTH: 16
<212> TYPE: DNA
<213> ORGANISM: Artificial
<220> FEATURE:
<223> OTHER INFORMATION: Synthetic

<400> SEQUENCE: 36
cgaccgtacc tagtcg                                                     16

<210> SEQ ID NO 37
<211> LENGTH: 16
<212> TYPE: DNA
<213> ORGANISM: Artificial
<220> FEATURE:
<223> OTHER INFORMATION: Synthetic

<400> SEQUENCE: 37
cctggtcaga ctcagg                                                     16
```